US006907887B2

(12) United States Patent
Conkling

(10) Patent No.: US 6,907,887 B2
(45) Date of Patent: Jun. 21, 2005

(54) MODIFYING NICOTINE AND NITROSAMINE LEVELS IN TOBACCO

(75) Inventor: Mark A. Conkling, Chapel Hill, NC (US)

(73) Assignee: Vector Tobacco Ltd., Hamilton, HMCX (BM)

( * ) Notice: Subject to any disclaimer, the term of this patent is extended or adjusted under 35 U.S.C. 154(b) by 29 days.

(21) Appl. No.: 10/729,121

(22) Filed: Dec. 5, 2003

(65) Prior Publication Data

US 2004/0144397 A1 Jul. 29, 2004

Related U.S. Application Data

(63) Continuation of application No. PCT/US02/18040, filed on Jun. 6, 2002.
(60) Provisional application No. 60/297,154, filed on Jun. 8, 2001.

(51) Int. Cl.[7] .................................................. A24D 1/04
(52) U.S. Cl. ........................ 131/364; 131/352; 131/270
(58) Field of Search ................................. 131/347, 364, 131/352, 270; 800/317.3

(56) References Cited

U.S. PATENT DOCUMENTS

| | | | |
|---|---|---|---|
| 2,479,526 | A | 8/1949 | Touton |
| 2,728,603 | A | 8/1955 | Helijo |
| 4,693,976 | A | 9/1987 | Schilperoort |
| 4,762,785 | A | 8/1988 | Comai |
| 4,821,747 | A | 4/1989 | Stuhl et al. |
| 4,885,248 | A | 12/1989 | Ahlquist |
| 4,940,838 | A | 7/1990 | Schilperoort et al. |
| 4,945,050 | A | 7/1990 | Sanford et al. |
| 4,954,442 | A | 9/1990 | Gelvin et al. |
| 5,034,322 | A | 7/1991 | Rogers et al. |
| 5,036,006 | A | 7/1991 | Sanford et al. |
| 5,100,792 | A | 3/1992 | Sanford et al. |
| 5,107,065 | A | 4/1992 | Shewmaker et al. |
| 5,149,645 | A | 9/1992 | Hoekema et al. |
| 5,190,931 | A | 3/1993 | Inouye et al. |
| 5,208,149 | A | 5/1993 | Inouye et al. |
| 5,231,020 | A | 7/1993 | Jorgensen et al. |
| 5,254,800 | A | 10/1993 | Bird et al. |
| 5,260,205 | A | 11/1993 | Nakatani et al. |
| 5,272,065 | A | 12/1993 | Inouye et al. |
| 5,283,184 | A | 2/1994 | Jorgensen et al. |
| 5,352,605 | A | 10/1994 | Fraley et al. |
| 5,356,799 | A | 10/1994 | Fabijanski et al. |

(Continued)

FOREIGN PATENT DOCUMENTS

| | | |
|---|---|---|
| CA | 1341091 | 9/2000 |
| DE | 1 917 52 | 12/1969 |
| DE | 2 203 105 | 11/1972 |
| EP | 0 116 718 A1 | 8/1984 |
| EP | 0 120 515 B1 | 10/1984 |
| EP | 0 120 515 A2 | 10/1984 |
| EP | 0 120 516 A2 | 10/1984 |
| EP | 0 131 620 B1 | 1/1985 |
| EP | 0 131 623 B2 | 1/1985 |
| EP | 0 131 624 B1 | 1/1985 |
| EP | 0 140 308 A2 | 5/1985 |
| EP | 0 140 308 A3 | 5/1985 |
| EP | 0 140 308 B1 | 5/1985 |
| EP | 0 159 779 B1 | 10/1985 |
| EP | 0 189 707 B1 | 8/1986 |
| EP | 0 223 399 A1 | 5/1987 |
| EP | 0 224 287 A1 | 6/1987 |
| EP | 0 240 208 B1 | 10/1987 |
| EP | 0 240 208 A3 | 10/1987 |
| EP | 0 240 208 A2 | 10/1987 |
| EP | 0 265 556 A1 | 5/1988 |
| EP | 0 270 822 A1 | 6/1988 |
| EP | 0 290 799 A2 | 11/1988 |

(Continued)

OTHER PUBLICATIONS

Adams et al., "Biogenesis and Chemistry of Alkaloid–Derived N–Nitrosamines," *Abstracts of Papers*, 184$^{th}$ ACS National Meeting, Kansas City, Missouri, Sep. 12–17, 1982.

Adams et al., "On the pharmacokinetics of tobacco–specific N–nitrosamines in Fischer rats," *Carcinogenesis*, 6:509–511 (1985).

Adams et al., "Pharmacokinetics of Tobacco–Specific N–Nitrosamines,", N–Nitroso Compounds: Occurrence, Biological Effects and Relevance to Human Cancer, Proceedings of the VIIIth International Symposium on N–Nitroso Compounds held in Banff, Canada, Sep. 5–9, 1983, IARC Scientific Publications No. 57, pp. 779–785.

Adams et al., "Tobacco–Specific N–Nitrosamines in Dry Snuff," *Fd Chem. Toxic.*, 25(3):245–246 (1987).

Adams et al., "Tobacco–Specific Nitrosamine Accumulation in Different Genotypes of Burley Tobacco at Different Stages of Growth and Air–Curing," *TCRC* (1987).

Adams et al., "Toxic and carcinogenic agents in undiluted mainstream smoke and sidestream smoke of different types of cigarettes," *Carcinogenesis*, 8(5):729–731 (1987).

Andersen et al., "Accumulation of 4–(N–Methyl–N–nitrosamino)–1–(3–pyridyl)–1–butanone in Alkaloid Genotypes of Burley Tobacco During Postharvest Processing: Comparisons with N'–Nitrosononicotine and Probable Nitrosamine Precursors," *Cancer Research*, 45:5287–5293 (1985).

(Continued)

*Primary Examiner*—Dionne A. Walls
(74) *Attorney, Agent, or Firm*—Knobbe Martens Olson & Bear LLP

(57) ABSTRACT

The present invention generally relates to tobacco and tobacco products having a reduced amount of nicotine and/or tobacco specific nitrosamines (TSNA). More specifically, several ways to make tobacco plants that have reduced nicotine and TSNA levels have been discovered. Embodiments include tobacco harvested from said tobacco plants, cured tobacco from said tobacco plants, tobacco products made with said cured tobacco and methods of making these compositions.

20 Claims, 6 Drawing Sheets

U.S. PATENT DOCUMENTS

| | | | | |
|---|---|---|---|---|
| 5,365,015 | A | 11/1994 | Grierson et al. | |
| 5,369,023 | A | 11/1994 | Nakatani et al. | |
| 5,451,514 | A | 9/1995 | Boudet et al. | |
| 5,453,566 | A | 9/1995 | Shewmaker et al. | |
| 5,459,252 | A | 10/1995 | Conkling et al. | |
| 5,464,763 | A | 11/1995 | Schilperoort et al. | |
| 5,501,967 | A | 3/1996 | Offringa et al. | |
| 5,530,196 | A | 6/1996 | Fraley et al. | |
| 5,610,288 | A | 3/1997 | Rubenstein | |
| 5,635,381 | A | 6/1997 | Hooykaas et al. | |
| 5,668,295 | A | 9/1997 | Wahab et al. | |
| 5,684,241 | A | 11/1997 | Nakatani et al. | |
| 5,693,512 | A | 12/1997 | Finer et al. | |
| 5,713,376 | A | 2/1998 | Berger | |
| 5,723,751 | A | 3/1998 | Chua | |
| 5,731,179 | A | 3/1998 | Komari et al. | |
| 5,759,829 | A | 6/1998 | Shewmaker et al. | |
| 5,767,378 | A | 6/1998 | Bojsen et al. | |
| 5,776,502 | A | 7/1998 | Foulkes et al. | |
| 5,776,771 | A | 7/1998 | Yu et al. | |
| 5,803,081 | A | 9/1998 | O'Donnell, Jr. et al. | |
| 5,810,020 | A | 9/1998 | Northway et al. | |
| 5,830,728 | A | 11/1998 | Christou et al. | |
| 5,834,236 | A | 11/1998 | Lamb et al. | |
| 5,837,876 | A | 11/1998 | Conkling et al. | |
| 5,845,647 | A | 12/1998 | O'Donnell, Jr. et al. | |
| 5,851,804 | A | 12/1998 | Snyder et al. | |
| 5,858,742 | A | 1/1999 | Fraley et al. | |
| 5,858,774 | A | 1/1999 | Malbon et al. | |
| 5,877,023 | A | 3/1999 | Sautter et al. | |
| 5,929,306 | A | 7/1999 | Torisky et al. | |
| 5,932,782 | A | 8/1999 | Bidney | |
| 5,962,768 | A | 10/1999 | Cornelissen et al. | |
| 5,976,880 | A | 11/1999 | Sautter et al. | |
| 5,981,839 | A | 11/1999 | Knauf et al. | |
| 5,989,915 | A | 11/1999 | Christou et al. | |
| 5,994,629 | A | 11/1999 | Bojsen et al. | |
| 6,022,863 | A | 2/2000 | Peyman | |
| 6,051,409 | A | 4/2000 | Hansen et al. | |
| 6,051,757 | A | 4/2000 | Barton et al. | |
| 6,135,121 | A | 10/2000 | Williams | |
| 6,153,811 | A | 11/2000 | Lowe et al. | |
| 6,165,715 | A | 12/2000 | Collins et al. | |
| 6,174,724 | B1 | 1/2001 | Rogers et al. | |
| 6,202,649 | B1 | 3/2001 | Williams | |
| 6,255,560 | B1 | 7/2001 | Fraley et al. | |
| 6,265,638 | B1 | 7/2001 | Bidney et al. | |
| 6,271,031 | B1 | 8/2001 | Falco et al. | |
| 6,281,410 | B1 | 8/2001 | Knauf et al. | |
| 6,303,847 | B1 | 10/2001 | Kawaoka et al. | |
| 6,350,479 | B1 | 2/2002 | Williams et al. | |
| 6,425,401 | B1 | 7/2002 | Williams | |
| RE38,123 | E | 5/2003 | Williams | |
| 2001/0006797 | A1 | 7/2001 | Kumagai et al. | |
| 2001/0026941 | A1 | 10/2001 | Hed et al. | |
| 2002/0174874 | A1 | 11/2002 | Williams | |
| 2003/0018997 | A1 * | 1/2003 | Conkling et al. | 800/317.3 |
| 2004/0103454 | A1 * | 5/2004 | Conkling et al. | 800/279 |

FOREIGN PATENT DOCUMENTS

| | | | |
|---|---|---|---|
| EP | 0 290 799 | A3 | 11/1988 |
| EP | 0 320 500 | A3 | 6/1989 |
| EP | 0 320 500 | A2 | 6/1989 |
| EP | 0 131 623 | B1 | 3/1991 |
| EP | 0 458 367 | B1 | 11/1991 |
| EP | 0 458 367 | A1 | 11/1991 |
| EP | 0 467 349 | B1 | 1/1992 |
| EP | 0 486 214 | A3 | 5/1992 |
| EP | 0 486 214 | A2 | 5/1992 |
| EP | 0 486 234 | B1 | 5/1992 |
| WO | WO 84/02913 | | 8/1984 |
| WO | WO 84/02919 | | 8/1984 |
| WO | WO 84/02920 | | 8/1984 |
| WO | 0 176 112 | B1 | 4/1986 |
| WO | 0 223 399 | B1 | 5/1987 |
| WO | WO 90/12084 | | 10/1990 |
| WO | WO 91/02070 | | 2/1991 |
| WO | WO 92/15680 | | 9/1992 |
| WO | WO 93/05163 | | 3/1993 |
| WO | WO 93/05646 | | 4/1993 |
| WO | WO 93/17116 | | 9/1993 |
| WO | WO 94/20627 | | 9/1994 |
| WO | WO 94/26913 | | 11/1994 |
| WO | WO 94/28142 | | 12/1994 |
| WO | WO 95/16031 | | 6/1995 |
| WO | WO 95/34668 | | 12/1995 |
| WO | WO 95/35388 | | 12/1995 |
| WO | WO 96/21725 | | 7/1996 |
| WO | WO 97/05261 | | 2/1997 |
| WO | WO 97/08330 | | 3/1997 |
| WO | WO 97/12046 | | 4/1997 |
| WO | WO 97/32016 | | 9/1997 |
| WO | WO 97/41892 | | 11/1997 |
| WO | WO 97/44450 | | 11/1997 |
| WO | WO 97/49727 | | 12/1997 |
| WO | WO 98/05757 | | 2/1998 |
| WO | WO 98/30701 | | 7/1998 |
| WO | WO 98/32843 | | 7/1998 |
| WO | WO9856923 | * | 12/1998 |
| WO | WO 98/56932 | | 12/1998 |
| WO | WO 99/10512 | | 3/1999 |
| WO | WO 99/14348 | | 3/1999 |
| WO | WO 99/25854 | | 5/1999 |
| WO | WO 99/32619 | | 7/1999 |
| WO | WO 99/32642 | | 7/1999 |
| WO | WO 99/49029 | | 9/1999 |
| WO | WO 99/53050 | | 10/1999 |
| WO | WO 99/61631 | | 12/1999 |
| WO | WO 00/12735 | | 3/2000 |
| WO | WO 00/18939 | | 4/2000 |
| WO | WO 00/29566 | | 5/2000 |
| WO | WO 00/37060 | | 6/2000 |
| WO | WO 00/37663 | | 6/2000 |
| WO | WO 00/63398 | | 10/2000 |
| WO | WO 00/67558 | | 11/2000 |
| WO | WO 01/09302 | | 2/2001 |
| WO | WO 01/38514 | | 5/2001 |
| WO | WO 01/44482 | | 6/2001 |
| WO | WO 01/49844 | | 7/2001 |
| WO | WO 01/51630 | A1 | 7/2001 |
| WO | WO 01/68836 | A2 | 9/2001 |
| WO | WO 01/77350 | A2 | 10/2001 |
| WO | WO 02/00927 | | 1/2002 |

OTHER PUBLICATIONS

Andersen et al., "Effect of Storage Conditions of Nitrosated, Acylated, and Oxidized Pyridine Alkaloid Derivatives in Smokeless Tobacco Products," *Cancer Research*, 49:5895–5900 (1989).

Andersen et al., "Effects of Air–Curing Environment on Alkaloid–Derived Nitrosamines in Burley Tobacco," *In Relevance of N'–Nitroso Compounds to Human Cancer: Exposure and Mechanisms*; Bartsch, H., O'Neill, I.K., Shultz–Hermann, R., Eds.; IARC Scientific Publication No. 84; World Health Organization; Lyon, 1987, pp. 451–455.

Andersen et al., "Levels of Alkaloids and Their Derivatives in Air– and Fire–Cured KY 171 Dark Tobacco During Prolonged Storage: Effects of Temperature and Moisture," *Tobacco Science*, 34:60–56 (1990).

Andersen et al., "N'–Acyl and N'–Nitroso Pyridine Alkaloids in Alkaloid Lines of Burley Tobacco during Growth and Air–Curing," *J. Agric. Food Chem.*, 37(1):44–50 (1989).

Andersen et al., "pH Changes in Smokeless Tobaccos Undergoing Nitrosation," *ACS Symposium Series 553*, Nitrosamines and Related N–Nitroso Compounds, 29:320–321 (1994).

Andersen et al., "Total Carbonyls and Phenols in Experimental Burley and Bright Tobacco," J. Agric. Food Chem., 27(4):891–895 (1979).

Atawodi et al., "Tobacco–specific nitrosamines in some Nigerian cigarettes," *Cancer Letters*, 97:106 (1995).

Bay et al., "The Nitrosation of Hexetidine and Hexetidine and Hexedine: Characterization of the Major Nitrosamine from Common Antimicrobial Agents," *Chem. Res. Toxicol.*, 7(6):868–876 (1994).

Beck et al, "Nucleotide Sequence and Exact Localization of the Neomycin Phosphotransferase Gene from Transposon Tn 5", *Gene*, 19: 327–336 (1982).

Bevan & Flavell, "A Chimaeric Antibiotic Resistance Gene as a Selectable Marker for Plant Cell Transformation", *Nature*, 304: 184–187 (1983).

Brittebo et al., "Metabolism of Tobacco–specific Nitrosamines by Cultured Rat Nasal Mucosa," *Cancer Research*, 43:4343–4348 (1983).

Brunnemann et al., "Analytical Studies on Tobacco–Specific N–Nitrosamines in Tobacco and Tobacco Smoke," *Toxicology*, 21(4):235–240 (1991).

Brunnemann et al., "Assessment of Carcinogenic Volatile N–Nitrosamines in Tobacco and in Mainstream and Sidestream Smoke from Cigarettes," *Cancer Research*, 37:3218–3222 (1977).

Brunnemann et al., "Assessment of the carcinogenic N–nitrosodiethanolamine in tobacco products and tobacco smoke," Carcinogenesis, 2(11):1123–1127 (1981).

Brunnemann et al., "Identification and analysis of a new tobacco–specific N–Nitrosamine, 4–(methylnitrosamino)–4–(3–pyridyl)–1–butanol," *Carcinogenesis*, 8(3):465–469 (1987).

Brunneman et al, "Isolation, Identification, and Bioassay of the Tobacco–Specific N–Nitrosamines, 4–(Methylnitrosamino)–4–(3–Pyridyl)–1–Butanal," Seventy–Ninth Annual Meeting of the American Association for Cancer Research, May 25–28, 1988, vol. 29.

Brunnemann et al., "N–Nitrosamines in Chewing Tobacco: An International Comparison," *J. Agric. Food Chem.*, 33(6):1178–1181 (1985).

Brunnemann et al., "N–Nitrosamines: Environmental Occurrence, In Vivo Formation and Metabolism," *J. Toxicol.–Clin. Toxicol.*, 19(6&7), pp. 661–688, Abstract No. 34, 183$^{rd}$ ACS National Meeting, Mar. 28, 1982–Apr. 2, 1982.

Brunnemann et al., "Recent Advances in Tobacco Science: Analytical Studies on N–Nitrosamines in Tobacco and Tobacco, Smoke," *Proceedings of a Symposium Presented at the 45$^{th}$ Meeting of the Tobacco Chemists' Research Conference*, vol. 17, Oct. 20, 1991–Oct. 23, 1991, The Grove Park Inn, Asheville, North Carolina.

Brunnemann et al., "Role of Tobacco Stems in the Formation of N–Nitrosamines in Tobacco and Cigarette Mainstream and Sidestream Smoke," *J. Agric. Food. Chem.*, 31(6):1221–1224 (1983).

Brunnemann et al., "Environmental Carcinogens Selected Methods of Analysis. II.2 Tobacco and Tobacco Smoke (Volatile and Tobacco–Specific Nitrosamines). II.2.c N–Nitrosodiethanolamine in Tobacco and Mainstream and Sidestream Smoke," World Health Organization, International Agency for Research on Cancer, IARC Publications No. 45, pp. 85–92 (1983).

Burton et al., "Accumulation of Tobacco–Specific Nitrosamines during Curing and Aging of Tobacco," ACS Symposium Series 553, Chapter 41, pp. 361–362, 204$^{th}$ National Meeting of the American Chemical Society, Washington, D.C., Aug. 23, 1992–Aug. 28, 1992.

Burton et al., "Changes in Chemical Composition of Burley Tobacco during Senescence and Curing. 1. Plastid Pigments," *J. Agric. Food Chem.*, 33(5):879–883 (1985).

Burton et al., "Changes in Chemical Composition of Burley Tobacco during Senescence and Curing. 2. Acylated Pyridine Alkaloids," *J. Agric. Food Chem.*, 36(3):579–584 (1988).

Burton et al, "Changes in Chemical Composition of Burley Tobacco during Senescence and Curing. 3. Tobacco–Specific Nitrosamines," *J. Agric. Food Chem.*, 37(2):426–430 (1989).

Burton et al., "Distribution of Tobacco Constituents in Tobacco Leaf Tissue. 1. Tobacco–Specific Nitrosamines, Nitrate, Nitrite, and Alkaloids, "*J. Agric. Food Chem.*, 40:1050–1058 (1992).

Burton et al., "Influence of Temperature and Humidity on the Accumulation of Tobacco Specific Nitrosamines in Stored Burley Tobacco," *J. Agric. Food Chem.*, 37:1372–1377 (1989).

Burton et al., "Relationship between Tobacco–Specific Nitrosamines and Nitrite from Different Air–Cured Tobacco Varieties," *J. Agric. Food Chem.*, 42(9):2007–2011 (1994).

Burton et al., "Topics Related to N–Nitrosamines and Their Precursors," *45$^{th}$ TCRC*, Oct. 20–23 (1991).

Burtin D. and Michael, A.J., "Over Expressions of Arginine Decarboxylase in Transgenic Plants," *Biochem J.*, 325(part2):331–337 (1997).

Burton et al., "Burley Tobacco—The Effects of Harvesting and Curing Procedures on the Composition of the Cured Leaf," *Tobacco Science*, 5:48–55 (1988).

Bush and Saunders, "Physiological Aspects of Genetic Variation in Nicotine Content in Tobacco (*Nicotiana tabacum*)," *Tobacco Abstract*, 23, p. 380 (1979).

Bush and Saunders, "Nicotine Biosynthetic Enzymes of Burley Tobacco," *Tobacco Abstracts*, 24, p. 260 (1980).

Bush et al., "Origin of nitrite–nitrogen for tobacco–specific N–nitrosamine formation," *Technologie–Agriculture*, No. 9814, p. 139 (1995).

Carmella et al., "Formation of hemoglobin adducts upon Treatment of F344 Rats with the Tobacco–specific Nitrosamines 4–(Methylnitrosamino)–1–(3–pyridyl)–1–butanone and N'–Nitrosonornicotine," *Cancer Research*, 47:2626–2630 (1987).

Carmella et al., "Mass Spectrometric Analysis of Tobacco–specific Nitrosamine Hemoglobin Adducts in Snuff Dippers, Smokers, and Nonsmokers," *Cancer Research*, 50:5438–5445 (1990).

Carmella et al., "Metabolite of the Tobacco–specific Nitrosamine 4–(Methylnitrosamino)–1–(3–pyridyl)–1–butanone in Smokers' Urine," *Cancer Research*, 53:721–724 (1993).

Castonguay et al., "Carcinogenicity, Metabolism and DNA Binding of the Tobacco Specific Nitrosomine, 4–(Methylnitrosamino)–1–(3–Pyridyl)–1–Butanone (NNK)," AACR Abstracts, vol. 22, No. 297 (1981).

Castonguay et al., "Metabolism of Tobacco–Specific Nitrosamines in Cultured Human Tissue," AACR Abstracts, Seventy–third Annual Meeting of the American Association, Apr. 28–May 1, 1982, vol. 23.

Chamberlain et al., "Chemical Composition of Nonsmoking Tobacco Products," *J. Agric. Food Chem.*, 36(1):48–50 (1988).

Chamberlain et al., "Curing Effects on Contents of Tobacco Specific Nitrosamines in Bright and Burley Tobaccos," USDA, ARS, pp. 1–41 (1986).

Chamberlain et al., "Effects of Curing and Fertilization on Nitrosamine Formation in Bright and Burley Tobacco," *Beltrage zur Tabakiorschung International*, 15(2):87–92 (1992).

Chamberlain et al., "Studies on the Reduction of Nitrosamines in Tobacco," *Tobacco Science*, 38:81–82 (1986).

Chaplin et al., "Catalog of the Tobacco Introductions in the U.S. Department of Agriculture's Tobacco Germplasm Collection (*Nicotiana tabacum*)," U.S. Department of Agriculture, Agricultural Research Service, Agricultural Reviews and Manuals, ARM–S–27, Oct. 1982.

Chilton et al., "Tailoring the Agrobacterium Ti Plasmid as a Vector for Plant Genetic Engineering", *Stadler Symp.*, 13: 39–53 (1981).

Colbere–Garapin et al., "A New Dominant Hybrid Selective Marker for Higher Eukaryotic Cells", *J. Mol. Biol.*, 150: 1–14 (1981).

Conkling et al., "Isolation of Transcriptionally Regulated Root–Specific Genes From Tobacco," *Plant Physiology*, 93(3):1203–121.1 (1990).

Cornelissen and Vandewiele, "Both RNA Level and Translation Efficiency Are Reduced by Anti–Sense RNA in Transgenic Tobacco," *Nucleic Acids Res.*, 17(3):833–843 (1989).

Crowley et al., *Cell*, 43:633–641 (1985).

Cuozzo et al., "Viral Protection in Transgenic Tobacco Plants Expressing the Cucumber Mosaic virus Coat Protein or Its Antisense RNA," *Biotechnology*, 6:549–557 (1988).

Database entry of Ensembl Human Genome Server, AC006461.2.1.181215, BLASTIN 2.0a13MP–WashU [Jun. 10, 1997], 2 pp.

Database entry of Ensembl Human Genome Server, AC024028.10.1.176278, BLASTIN 2.0a13MP–WashU [Jun. 10, 1997], 3 pp.

Database entry of Ensembl Human Genome Server, AC069205.6.1.132242, BLASTIN 2.0a13MP–WashU [Jun. 10, 1997], 1 pp.

Database entry of Ensembl Human Genome Server, AC097498.3.1.144511, BLASTN 2.0a13MP–WashU [Jun. 10, 1997], 1 pp.

Database entry of Ensembl Human Genome Server, AC104785.4.111369.213599, BLASTN 2.0a13MP–WashU [Jun. 10, 1997], 1 pp.

Database entry of Ensembl Human Genome Server, AC105416.3.1.123331, BLASTN 2.0a13MP–WashU [Jun. 10, 1997], 1 pp.

Database entry of Ensembl Human Genome Server, AC108146.3.1.91810, BLASTN 2.0a13MP–WashU [Jun. 10, 1997], 1 pp.

Database entry of Ensembl Human Genome Server, AC115109.2.1.59356, BLASTN 2.0a13MP–WashU [Jun. 10, 1997], 1 pp.

Davies and Jimenez, "A New Selective Agent for Eukaryotic Cloning Vectors", *Am. J. Trop. Med. Hyg.*, 29(5):1089–1092 (1980).

Delauney et al., "A Stable Bifunctional Antisense Transcript Inhibiting Gene Expression in Transgenic Plants," *Proc. Natl. Acad. Sci.* USA, 85:4300–4304 (1988).

Depicker et al., "Nonpaline Synthase: Transcript Mapping and DNA Sequence", *Journal of Molecular and Applied Genetics*, 1(6): 561–573 (1982).

Djordjevic et al., "Accumulation and Distribution of Acylated Nornicotine Derivatives in Flue–Cured Tobacco Alkaloid Isolines," *J. Agric Food Chem.*, 28(2):347–350 (1990).

Djordjevic et al., "Assessment of major Carcinogens and Alkaloids in the Tobacco and Mainstream Smoke of USSR Cigarettes," *Int. J. Cancer*, 47:348–351 (1991).

Djordjevic et al., "The need for Regulation of Carcinogenic N–Nitrosamines in Oral Snuff," *Fd. Chem. Toxic.*, 31(7):497–501 (1993).

Djordjevic et al., "Tobacco–Specific Nitrosamine Accumulation and Distribution in Flue–Cured Tobacco Alkaloid Isolines," *J. Agric. Food Chem.*, 37(3):752–756 (1989).

Doerr–O'Rourke et al., "Effect of phenethyl isothiocyanate on the metabolism of the tobacco–specific nitrosamine 4–(methylnitrosamino)010(3–pyridyl)–1–butanone by cultured rat lung tissue," Carcinogenesis, 12(6):1029–1034 (1991).

Ecker and Davis, "Inhibition of Gene Expression In Plant Cells by Expression of Antisense RNA," *Proc. Natl. Acad. Sci.* USA, 83:5372–5376 (1986).

Finster, P., "N–Nitrosamines in Tobacco Products," FE–Report No. 101E, Literature Study, Project No. 0603, pp. 1–53, Sep. 1986.

Fischer et al., "Improved Method for the Determination of Tobacco–Specific Nitrosamines (TSNA) in Tobacco Smoke," Beitrage zur Tabakforschung International, 14(3):145–153 (1989).

Fischer et al., "Influence of Smoking Parameters on the Delivery of Tobacco–Specific Nitrosamines in Cigarette Smoke—a Contribution to Relative Risk Evaluation," *Carcinogenesis*, 10(6):1059–1066 (1989).

Fischer et al., "Investigations on the origin of tobacco–specific nitrosamines in mainstream smoke of cigarettes," *Carcinogenesis*, 11(5):723–730 (1990).

Fischer et al., "Preformed tobacco–specific nitrosamines in tobacco–role of nitrate and influence of tobacco type," Carcinogenesis, 10(8):1511–1517 (1989).

Fischer et al., "Tobacco–specific nitrosamines in mainstream smoke of West German cigarettes–tar alone is not a sufficient index for the carcinogenic potential of cigarette smoke," Carcinogenesis, 10(1):169–173 (1999).

Fischer et al., "Tobacco–specific nitrosamines in Canadian cigarettes," J. Cancer Res. Clin. Oncol., 116:563–568 (1990).

Fischer et al., "Tobacco–specific nitrosamines in European and USA cigarettes," Arch. Geschwulstforsch., 60 (1990) Heft 3, pp. 169–177.

Fischer et al., "Tobacco–specific nitrosamines in Commercial cigarettes: Possibilities for reducing exposure," Relevance to Human Cancer of N–Nitroso Compounds, Tobacco Smoke and Mycotoxins, ed. I.K. O'Neill, J. Chen and H. Bartsch Lyon, International Agency for Research on Cancer, IARC, pp. 489–492 (1991).
Foiles, et al., "Mass Spectrometric Analysis of Tobacco–Specific Nitrosamine–DNA Adducts in Smokers and Nonsmokers," *Chem. Res. Toxic.*, 4:364–368 (1991).
Fraley et al., "Expression of Bacterial Genes in Plant Cells", *Proc. Natl. Acad. Sci.* USA, 80: 4803–4807 (1983).
Fraley et al., "Use of a Chimeric Gene to Confer Antibiotic Resistance to Plant Cells", *Advances in Gene Technology: Molecular Genetics of Plants and Animals*, 20:211–221 (1983).
Framond et al., "Mini–Ti: A New Vector Strategy for Plant Genetic Engineering", *Biotechnology*, 5:262–269 (1983).
Genbank entry AB005879. *Nicotania tabacum* mRNA for BYJ6, Feb. 5, 1999, 2pp.
Genbank entry AC002131. *Arabidopsis thaliana* chromosome 1 BAC F12F1 sequence, May 28, 1998, 38 pp.
Genbank entry AC006461. *Homo sapiens* BAC clone RP11–343N14 from 2, Mar. 1, 2002, 65 pp.
Genbank entry AB024028. *Homo sapiens* BAC clone RP11–151M24 from 7, Nov. 7, 2001, 68 pp.
Genbank entry AC069205. *Homo sapiens* BAC clone RP11–735P12 from 2, Jan. 9, 2002, 46 pp.
Genbank entry AC079141. *Homo sapiens* BAC clone RP11–502A23 from 4, Nov. 7, 2001, 43 pp.
Genbank entry AC097498 *Homo sapiens* BAC clone RP11–326N15 from 4, Mar. 1, 2002, 51pp.
Genbank entry AC105416. *Homo sapiens* BAC clone RP11–310A13 from 4, Jun. 12, 2002, 47 pp.
Genbank entry AC108146. *Homo sapiens* BAC clone RP11–437H3 from 2, Mar. 9, 2002, 35 pp.
Genbank entry AC115109. *Homo sapiens* BAC clone RP11–78110 from 2, May 29, 2002, 23 pp.
Genbank entry AR164048. Sequence 7 from patent US 6271031, Oct. 17, 2001, 1 pp.
Genbank entry AR164050. Sequence 11 from patent US 6271031, Oct. 17, 2001, 1pp.
Genbank entry AX344860. Sequence 285 from patent US WO0200927, Feb. 1, 2002, 4pp.
Genbank entry U27809. Peanut bud necrosis virus S segment non–structural protein and nucleocapsid protein genes, Jul. 23, 1996, 3 pp.
Gondwe et al., "Screening Tobacco Types, Cultivars and Curing Methods for Low Nitrosamine Tobacco Production in Malawi," Agricultural Research and Extension Trust, 1996 Coresta Congress at Yokohama Japan, Nov. 3–8, 1996.
Hamill et al., "Over–expressing a Yeast Ornithine Decarboxylase Gene in Transgenic Roots of *Nicrotiana rustica* Can Lead to Enhanced Nicotine Accumulation," *Plant Molecular Biology*, 15:27–37 (1990).
Hecht et al., "A study of tobacco carcinogenesis XLII. Bioassay in A/J mice of some structural analogues of tobacco–specific nitrosamines," *Cancer Letters*, 42:141–145 (1988).
Hecht et al., "Biochemistry, Biology, and Carcinogenicity of Tobacco–Specific N–Nitrosamines," *Chem. Res. Toxic.*, 11(6):559–603 (1998).
Hecht et al., "Biomarkers for Human Uptake and Metabolic Activation of Tobacco–specific Nitrosamines," *Cancer Research* (suppl), 54:1912–1917 (1994).
Hecht et al., "Chemical Studies on Tobacco Smoke. XXXIII. N'–Nitrosonornicotine in Tobacco: Analysis of Possible Contributing Factors and Biologic Implications," *J. Natl. Cancer*, 54(5):1237–1244 (1974).
Hecht et al., "Comparative Carcinogenicity of o–Toluidine Hydrochloride and o–Nitrosotoluene in F–344 Rats," *Cancer Letters*, 16:103–108 (1982).
Hecht et al., "Comparative Carcinogenicity in F344 Rats of the Tobacco–specific Nitrosamines, N'–Nitrosonornicotine and 4–(N–Methyl–N–nitrosamino)–1–(3–pyridyl)–1–butanone," *Cancer Research*, 40:298–302 (1980).
Hecht "Cyclic and Tobacco–Specific Nitrosamines: Metabolism and Macromolecular Adduct Formation," *American Chemical Society*, Abstract No. 68, $204^{th}$ ACS National Meeting, Washington, DC, Aug. 23, 1992–Aug. 28, 1992.
Hecht, "DNA adduct formation from tobacco–specific N–nitrosamines," *Mutation Research*, 424:127–142 (1999).
Hecht et al., "Endogenous Nitrosation of Tobacco Alkaloids in Rats," *American Chemical Society*, Abstract No. 64, $212^{th}$ ACS National Meeting, Aug. 25, 1996–Aug. 29, 1996.
Hecht et al., "Environmental Carcinogens Selected Methods of Analysis. II.2 Tobacco and Tobacco Smoke (Volatile and Tobacco–Specific Nitrosamines). II.2.d Tobacco–Specific Nitrosamines in Tobacco and Tobacco Smoke," World Health Organization, International Agency for Research on Cancer, IARC Publications No. 45, pp. 93–101 (1983).
Hecht et al., "Environmental Carcinogens Selected Methods of Analysis. IV.6 HPLC–TEA of Tobacco Specific Nitrosamines," World Health Organization, International Agency for Research on Cancer, IARC Publications No. 45, pp. 429–436 (1983).
Hecht et al., "Evidence for 4–(3–pyridyl)–4–oxobutylation of DNA in F344 rats treated with the tobacco–specific nitosamines 4–(methylnitrosomino)–1–(3–pyridyl)–1–butanone and N–nitrosonornicotine," *Carcinogenesis*, 9(1):161–165 (1988).
Hecht et al., "Induction of Oral Cavity Tumors in F344 Rats by Tobacco–specific Nitrosamines and Snuff," *Cancer Research*, 46:4162–4166 (1986).
Hecht et al., "Metabolism of the tobacco–specific nitrosamine 4–(methylnitrosamino)–1–(3–pyridyl)–1–butanone in the patas monkey: pharmacokinetics and characterization of glucuronide metabolites," *Carcinogenesis*, 14(2):229–236 (1993).
Hecht et al. "N–Nitroso Compounds: The Metabolism of Cyclic Nitrosamines," *A.C.S. Symposium Series*, 174(4):49–75 (1981).
Hecht et al., "Reaction of Nicotine and Sodium Nitrite: Formation of Nitrosamines and Fragmentation of the Pyrrolidine Ring," *J. Org. Chem.*, 43(1):72–76 (1978).
Hecht et al., "Recent Studies on the Metabolic Activiation of Tobacco–Specific Nitrosamines," *American Chemical Society*, Abstract No. 12, $217^{th}$ ACS National Meeting, Mar. 21, 1999–Mar. 25, 1999.
Hecht et al., "N–Nitroso Compounds: The Metabolism of Cyclic Nitrosamines," A.C.S. Symposium Series 174(4):50–75 (1981).
Hecht et al., "The relevance of tobacco–specific nitrosamines to human cancer," Cancer Surveys, 8(2):272–294 (1989).

Hecht et al., "Tobacco–Specific Nitrosamine Adducts: Studies in Laboratory Animals and Humans," *Environmental Health Perspectives*, 99:57–63 (1993).

Hecht et al., "Tobacco–specific nitrosamines, an important group of carcinogens in tobacco and tobacco smoke," *Carcinogenesis*, 9(6):875–884 (1988).

Hecht et al., "Tobacco–Specific Nitrosamines: Formation From Nicotine In Vitro and During Tobacco Curing and Carcinogenicity in Strain A Mice," *J. Natl. Cancer*, 60(4):819–824 (1978).

Hecht et al., "Tobacco–Specific Nitrosamines: Occurrence, Formation, Carcinogenicity, and Metabolism," *Accounts of Chemical Research*, 12:92–98 (1979).

Hermaisteens et al., "The Agrobacterium Tumefaciens Ti Plasmid as a Host Vector System for Introducing Foreign DNA in Plant Cells", *Nature*, 287: 654–656 (1980).

Herrera–Estrella et al., "Chimeric Genes as Dominant Selectable Markers in Plant Cells", *The Embo Journal*, 2(6): 987–995 (1993).

Herrera–Estrella et al., "Expression of Chimeric Genes Transferred into Plant Cells Using a Ti–Plasmid–Derived Vector", *Nature*, 303: 209–213 (1983).

Hibi et al., "Gene Expression in Tobacco Low–Nicotine Mutants," *Plant Cell*, 6:723–735 (1994).

Hoffmann, "Assessment of Tobacco–Specific N–Nitrosamines in Tobacco Products," *Cancer Research*, 39:2505–2509 (1979).

Hoffmann et al., "Carcinogenic Tobacco–specific N–Nitrosamines in Snuff and in the Saliva of Snuff Dippers," *Cancer Research*, 41:4305–4308 (1981).

Hoffmann et al, "Chemical Studies on Tobacco Smoke. XXVI. On the Isolation and Identification of Volatile and Non–Volatile N–Nitrosamines and Hydrazines in Cigarette Smoke," ZARC Sci.Pub. 9. L39–165. (1974).

Hoffman et al., "Environmental Carcinogens Selected Methods of Analysis. II.2 Tobacco and Tobacco Smoke (Volatile and Tobacco–Specific Nitrosamines). II.2.b Volatile Nitrosamines in Tobacco and Mainstream and Sidestream Smoke and Indoor Environments," World Health Organization, International Agency for Research on Cancer, *IARC Publications*, No. 45, pp. 69–83 (1983).

Hoffmann et al., "Formation, Occurrence and Carcinogenicity of N–Nitrosamines in Tobacco Products," *N–Nitroso Compounds*, Scanlan and Tannenbaum, eds., *ACS Symposium Series 174* (1981).

Hoffmann et al., "Formation, of Tobacco–Specific N–Nitrosamines, Their Carcinogenicity, and the Role of Dietary Fat in Their Carcinogenicity," *Abstracts of Papers*, Part 1, $204^{th}$ ACS National Meeting, Washington, DC, Aug. 23–28, 1992.

Hoffmann et al., "Formation and Analysis of N–Nitrosamines in Tobacco Products and Their Endogenous Formation in Consumers," N–Nitroso Compounds: Occurrence, Biological Effects and Relevance to Human Cancer, Proceedings of the VIIIth International Symposium on N–Nitroso Compounds held in Banff, Canada, Sep. 5–9, 1983, IARC Scientific Publications No. 57, pp. 743–762.

Hoffmann et al., "Introduction Tobacco–Specific N–Nitrosamines (TSNA)," *Critical Reviews in Toxicology*, Abstract, vol. 21, Issue 4 (1991).

Hoffmann et al., "Nicotine–derived N–Nitrosamines and Tobacco–related Cancer: Current Status and Future Directions," *Cancer Research*, 45:935–944 (1985).

Hoffman et al., "Nicotine–Derived N–Nitrosamines (TSNA) and Their Relevance in Tobacco Carcinogenesis," *Critical Reviews in Toxicology*, 21(4):305–311 (1991).

Hoffmann et al, "NICOTINE: A Precursor for Carcinogens," *Cancer Letters*, 26:67–75 (1985).

Hoffmann et al, "On the Endogenous Formation of N–Nitrosamines in Cigarette Smokers," AACR Abstracts, Seventy–Fourth, Annual Meeting of the American Association for Cancer Research, May 25–28, 1993, vol. 24.

Hoffmann et al., "Origin in Tobacco Smoke of N'–Nitrosonornicotine, a Tobacco–Specific Carcinogen: Brief Communication," *J. Nat. Cancer Inst.*, 58:1841–1844 (1977).

Hoffmann et al., "The Role of Volatile and Nonvolatile N–Nitrosamines in Tobacco Carcinogenesis," *Banbury Report*, Cold Spring Harbor laboratory, pp. 113–127 (1980).

Hoffmann et al., "Tobacco–Specific N–Nitrosamines and Areca–Derived N–Nitrosamines: Chemistry, Biochemistry, Carcinogenicity, and Relevance to Humans," *Journal of Toxicology and Environmental Health*, 41:1–52 (1994).

Hoffman et al., "Tobacco Specific N–Nitrosamines: Occurrence and Bioassays," *N–Nitroso Compounds: Occurrence and Biological Effects*, Proceedings of the VIIth International Symposium on N–Nitroso Compounds held in Tokyo, Sep. 28–Oct. 1, 1981, pp. 309–318.

Hoffman et al., "II.2 Tobacco and Tobacco Smoke (Volatile and Tobacco–Specific Nicotine) II.2.a General Aspects," *Environmental Carcinogens Selected Methods of Analysis*, vol. 6—N–Nitroso Compounds, pp. 63–67, International Agency for Research on Cancer, Lyon (1983).

Hoffman et al., "IV.2.b GC–Tea of Volatile Nitrosamines From Tobacco Products," *Environmental Carcinogens Selected Methods of Analysis*, vol. 6—N–Nitroso Compounds, IARC Publications No. 45 (1983).

Hoffmann et al., "Formation of Tobacco–Specific Nitrosamines: Carcinogenicity and the Role of Dietary Fat in Their Carcinogenicity," *American Chemical Society*, 21:266–278 (1994).

Holmberg et al., "Transgenic tobacco expressing Vitreoscilla Hemoglobin Exhibits Enhanced Growth and Altered Metabolite Production," *Nature Biotechnology*, 15:244–247 (1997).

Hooykaas et al., "The Ti–Plasmid of Agrobacterium Tumefaciens: A Natural Genetic Engineer", *TIBS*, 307–309 (1985).

Horsch et al., "A Simple and General Method for Transferring Genes into Plants," *Biological Sciences*, 227:1229–1231 (1985).

Hughes et al., "The Salmonella Typhimurium nadC Gene: Sequence Determination by use of Mud–P22 and Purification of Quinolinate Phosphoribosyltransferase," *J. Bacteriology*, 175(2):479–486 (1993).

Imanishi et al., "Differential Induction by Methyl Jasmonate of Genes Encoding Ornithine Decarboxylase and Other Enzymes Involved in Nicotine Biosynthesis in Tobacco Cell Cultures", *Plant Molecular Biology*, 38:1101–1111 (1998).

Irwin, W.D.E., "Comments on a Recent Paper by Fischer and Co–Workers Entitled "Tobacco–Specific Nitrosamines in Canadian Cigarettes"," pp. 1–14 (1991).

Izant and Weintraub, "Constitutive and Conditional Suppression of Exogenous and Endogenous Genes by Anti–Sense RNA," *Science*, 229:345–352 (1985).

Izant and Weintraub, "Inhibition of Thymidine Kinase Gene Expression by Anti–Sense RNA: A Molecular Approach to Genetic Analysis," *Cell*, 36:1007–1015, (1984).

Johnson et al., "N–Nitrosamines in Smoke Condensate From Several Varieties of Tobacco," *Journal of the National Cancer Institute*, 48(6):1845–1847 (1972).

Kim and Wold, "Stable Reduction of Thymidine Kinase Activity in Cells Expressing High Levels of Anti–Sense RNA," *Cell*, 42:129–138 (1985).
Kumar et al., "Tobacco–Specific N–Nitrosamines in Tobacco and Mainstream Smoke of Indian Cigarettes," *Fd. Chem. Toxic.*, 29(6):405–407 (1991).
Lam et al., "Site–Specific Mutations Alter in Vitro Factor Binding and change Promoter Expression Pattern in Transgenic Plants," *Proc. Natl. Acad. Sci.* USA, 86:7890–7894 (1989).
Larson et al., "Polycyclic Aromatic Hydrocarbons and volatile N–Nitrosamines in Some Dried Agricultural Products," *Swedish J. Agric. Res.*, 20(2):49–56 (1990).
Lichtenstein, "Anti–sense RNA as a Tool to Study Plant Gene Expression," *Nature*, 333:801–802 (1988).
Lorz et al., "Transformation Studies Using Synthetic DNA Vectors Coding For Antibiotic Resistance", *Plant Tissue Culture*, 511–512 (1982).
MacKown et al., "Tobacco–Specific N–Nitrosamines: Effect of Burley Alkaloid Isolines and Nitrogen Fertility Management," *J. Agric. Food Chem.*, 32(6):1269–1272 (1984).
MacKown et al., "Tobacco–Specific N–Nitrosamines: Formation during Processing of Midrib and Lamina Fines," *J. Agric. Food Chem.*, 36(5):1031–1035 (1988).
McCoy et al., "Influence of Chronic Ethanol Consumption on the Metabolism and Carcinogenicity of Tobacco–Related Nitrosamines," *N–Nitroso Compounds: Occurrence and Biological Effects*, Proceedings of the VIIth International Symposium on N–Nitroso Compounds held in Tokyo, Sep. 28–Oct. 1, 1981, IARC Scientific Publications No. 41, International Agency for Research on Cancer, Lyon (1982).
McGarry and Lindquist, *Proc. Natl. Acad. Sci.* USA, (1986).
Melton, "Injected Anti–Sense RNAs Specifically Block Messenger RNA Translation In Vivo," *Proc. Natl. Acad. Sci.* USA, 82:144–148 (1985).
Meliklan et al., "Volatile Nitrosamines: Analysis in Breast Fluid and Blood of Non–Lactating Women," *Fd Cosmet. Toxicol.*, 19:757–759 (1981).
Mirvish et al., "Ascorbate–Nitrite Reaction: Possible Means of Blocking the Formation of Carcinogenic N–Nitroso Compounds," *Science*, 177:65–68 (1972).
Mingwu et al., "Effect of Maleic Hydrazide Application on Accumulation of Tobacco–Specific Nitrosamines in Air–Cured Burley Tobacco," *J. Agric. Food Chem.*, 42:2912–2918 (1994).
Mingwu, Cui "The Source and the Regulation of Nitrogen Oxide Production for Tobacco–Specific Nitrosamine Formation During Air–Curing Tobacco," Dissertation, University of Kentucky (1998).
Mitacek et al., "Volatile nitrosamines and tobacco–specific nitrosamines in the smoke of Thai cigarettes: a risk factor for lung cancer and a suspected risk factor for liver cancer in Thailand," *Carcinogenesis*, 20(1):133–137 (1999).
Mizuno et al., "A Unique Mechanism Regulating Gene Expression: Translational Inhibition By a Complementary RNA Transcript (micRNA)," *Trends in Genetics*, 1:22–25 (1985).
Nair et al., "Carcinogenic Tobacco–Specific Nitrosamines in Indian Tobacco Products," *Fd Chem. Toxic.*, 27(11):751–753 (1989).
Nair et al., "Tobacco–Specific N–Nitrosamines [TSNA] in Green Mature and Processed Tobacco Leaves from India," *Beitrage zur Tabakforschung International*, 14(1):29–32 (1987).
Ohta Yatazawa, "Metabolic Key Step Discriminating Nicotine Producing Tobacco Callus Strain rom Ineffective One," *Biochem. Physiol. Pflanzen*, 175:382–385 (1980).
Osterdahl et al., "N–Nitrosamines in snuff and chewing tobacco on the Swedish market in 1983," *Food Additives and Contaminants*, 1(4):299–305 (1984).
Osterdahl et al., "Volatile N–Nitrosamines in Snuff and Chewing Tobacco on the Swedish Market," *Fd. Chem. Toxic.*, 21(6):759–762 (1983).
Perini, F.R., "Experimental Cigarette Tobacco column Tobacco Specific Nitrosamine (TSNA) Concentrations: A Comparison Among Single Blend Component Cigarettes and the #1580 Control Cigarette," Memorandum dated Oct. 26, 1989 to J.H. Bell.
Pestka et al., "Anti–mRNA: Specific Inhibition of Translation of Single mRNA Molecules," *Proc. Natl. Acad. Sci.* USA, 81:7525–7528 (1984).
Peterson et al., "Formation of NADP(H) Analogs of Tobacco–Specific Nitrosamines in Rat Liver and Pancretic Microsomes," Chem. Res. Toxicol., 7(5):599–608 (1994).
Peterson et al., "Quantitation of Microsomal α–Hydroxylation of the Tobacco–specific Nitrosamine, 4–(Methylnitrosamino)–1–(3–pyridyl)–1–butanone," *Cancer Research*, 51:5495–5500 (1991).
Poulsen et al., "Dissection of 5' Upstream Sequences for Selective Expression of the *Nicotiana plumbaginifolia* rbcS–8B gene," *Mol. Gen. Genet.*, 214:16–23 (1988).
Preiss et al., "Molecular Genetics of Kruppel, A Gene Required for Segmentation of the Drosophila Embryo," *Nature*, 313:27–32 (1985).
Preston–Martin, Susan, "Evaluation of the Evidence That Tobacco–Specific Nitrosomines (TSNA) Cause Cancer in Humans," Toxicology, 21(4):295–298 (1991).
Prokopczyk et al., "Significance of Nitrosamines in Betel Quid Carcinogenesis," ACS Symposium Series 553, *Nitrosamines and Related N–Nitroso Compounds*, Aug. 23–28, 1992.
Prokopczyk et al., "Supercritical Fluid Extraction in the Determination of Tobacco–Specific N–Nitrosamines in Smokeless Tobacco," Chem. Res. Toxicol., 5(3):336–340 (1992).
Results of search of Genbank Database, BLASTN 2.2.3 [Apr. 24, 2002], RID:1026175671–06698–1397, 15pp.
Results of search of Genbank Database, BLASTN 2.2.3 [Apr. 24, 2002], RID:1026319792–012476–25945, 30pp.
Rezaian et al, "Anti–Sense RNAs of Cucumber Mosaic Virus in Transgenic Plants Assessed for Control of the Virus," *Plant Molecular Biology*, 11:463–471 (1988).
Rivenson et al., "A Study of Tobacco Carcinogenesis XLIV. Bioassay in A/J Mice of Some N–Nitrosamines," *Cancer Letters*, 47:111–114 (1989).
Rivenson et al., "Carcinogenicity of Tobacco–Specific N–Nitrosamines (TSNA): The Role of the Vascular Network in the Selection of Target Organs," *Toxicology*, 21(4):255–264 (1991).
Rivenson et al., "Induction of Lung and Exocrine Pancreas Tumors in F344 Rats by Tobacco–specific and Areca–derived N–Nitrosamines," *Cancer Research*, 48:6912–6917 (1988).
Rivenson et al., "Observations on Lung Tumors Arising From MetaPlastic Squamous Epithelium in Rats Treated Chronically With The Tobacco–Specific Nitrosamines, 4–(Methylnitrosamino)–1–(3–Pyridyl)–1–Butamone (NNK)," Seventy–Ninth Annual Meeting of the American Association for Cancer Research, May 25–28, 1988, vol. 29.
Rivenson et al., "Pathogenic Considerations on Nasal Cavity Tumours Induced by Tobacco Specific Nitrosames (TSNA) in Rats," *European Journal of Cancer & Clinical Oncology*, Abstracts, p. 1312 (1983).

Rodermel et al., "Nuclear–Organelle Interactions: Nuclear Antisense Gene Inhibits Ribulose Bisphosphate Corboxylase Enzyme Levels in Transformed Tobacco Plants," *Cell*, 55:673–681 (1988).

Rosenberg et al., "Production of Phenocopies By Kruppel Antisense RNA Injection into Drosophila Embryos," *Nature*, 313–703–706 (1985).

Rothstein et al., "Stable and Heritable Inhibition of the Expression of Nopaline Synthase Tobacco Expressing Antisense RNA," *Proc. Natl. Sci.* USA, 84:8439–8443 (1987).

Rühl et al., "Chemical Studies on Tobacco Smoke LXVI. Comparative Assessment of Volatile and Tobacco–Specific N–Nitrosamines in the Smoke of Selected Cigarettes from the U.S.A., West Germany and France," *Journal of Analytical Toxicology*, 4:255–259 (1980).

Sandler et al., "Inhibition of Gene Expression in Transformed Plants by Antisense RNA," *Plant Molecular Biology*, 11:301–310 (1988).

Satyanarayana et al., "Peanut Bud Necrosis Tospovirus S RNA: Complete Nucleotide Sequence, Genome Organization and Homology to Other Tospoviruses",*Arch. Virol.* 141 (1), 85–98 (1996).

Saunders and Bush, "Comparison of Nicotine Biosynthesis Enzymes in Noctine.Level Genotypes of Burley Tobacco," *Agronomy Abstracts*, p. 84 (1978).

Schroth et al., "Tobacco–Specific Nitrosamines," Research and Development, Neuchatel—Quarterly Report, pp. 1–8, Apr.–Jun. 1994.

Sheehy et al., "Reduction of Polygalacturonase Activity in Tomato Fruit by Antisense RNA," *Proc. Natl. Acad. Sci.* USA, 85:8805–8809 (1988).

Schmeltz et al., "Nitrogen–Containing Compounds in Tobacco and Tobacco Smoke," *Chemical Reviews*, 77(3):295–311 (1977).

Smith et al., "Antisense RNA Inhibition of Polygalacturonase Gene Expression in Transgenic Tomatoes", *Nature*, 334: 724–726 (1988).

Song, Molecular Characterizations of Two Tobacco Root–Specific Genes: TobRB7 and NtQPTI, (1997) 224pp. Avail: UMI, Order No. DA9804246 from: Diss. Abstr. Int., B 1998, 58(8), 4061 XP002080228.

Spiegelhalder et al., "A Method for Determination of Tobacco–Specific Nitrosamines, Nitrate and Nitrite in Tobacco Leaves and Processed Tobacco," *Beitrage zur Tabakforschung International*, 14(3):135–144 (1989).

Spiegelhalder et al., "Formation of Tobacco–Specific Nitrosamines," *Critical Reviews in Toxicology*, Abstract, vol. 21, Issue 4, p. 241 (1991).

Spiegelhalder et al., "Tobacco–Specific Nitrosamines," *European Journal of Cancer Prevention*, 5(sup.1):33–38 (1996).

Stedman, "The Chemical Composition of Tobacco and Tobacco Smoke," *Chemical Reviews*, 68:153–207 (1968).

The Sanger Centre, "Toward a Complete Human Genome Sequence", *Cold Spring Harbor Laboratory Press*, 1097–1108, (1988).

Theologis et al., "Sequence and Analysis of Chromosome 1 of the Plant *Arabidopsis thaliana", Nature*, 408: 816–820 (2000).

Travers, "Regulation by Anti–Sense RNA," *Nature*, 310, p. 410 (1984).

Tricker et al., "The Occurrence of N–Nitro Compounds in zarda tobacco," *Cancer Letters*, 42:113–118 (1988).

Tricker et al., "The Occurrence of Tobacco–Specific Nitrosamines in Oral Tobacco Products and Their Potential Formation Under Simulated Gastric Conditions," *Fd Chem. Toxic.*, 26(10):861–865 (1988).

Trushin et al., "Stereoselective Metabolism of Nicotine and Tobacco–Specific N–Nitrosamines to 4–Hydroxy–4–(3–pyridyl)butonoic Acid in Rats," *Chem. Res. Toxicol.* 12(2):164–171 (1999).

Tso, T.C., "Production, Physiology, and Biochemistry of Tobacco Plant: Organic Metabolism–Alkaloids H. Tobacco Specific N–Nitrosamines," Ideals, Inc., pp. 467–486 (1990).

Upadhyaya et al., "Preparation of Pyridine–N–glucuronides of Tobacco–Specific Nitrosamines," *Chem. Res. Toxicol.*, 14(5):555–561 (2001).

Van der Kroll et al., "An Anti–Sense Chalcone Synthase Gene In Transgenic Plants Inhibits Flower Pigmentation," *Nature*, 333:866–869 (1988).

Van der Kroll et al., "Modulation of Eukaryotic Gene Expression by Complementary RNA or DNA Sequences," *Biotechniques*, 6:958–976 (1988).

Van der Kroll et al., "Antisense Genes in Plants: An Overview," *Gene*, 72:45–50 (1988).

Wagner et al., "The Regulation of Enzyme Activities of the Nicotine Pathway in Tobacco," *Physiol. Plantarum*, 68:667–672 (1986).

Wagner et al., "Determination of quinolinic acid phosphoribosyltransferase in tobacco, " *Phytochemistry*, vol. 23, No. 9, pp. 1881–1883 (1984).

Wang et al., "Right 25 bp Terminus Sequence of the Nopaline T–DNA is Essential for and Determines Direction of DNA Transfer from Agrobacterium to the Plant Genome", *Cell*, 38: 455–462 (1984).

Weintraub et al., "Anti–sense RNA as a Molecular Tool for Genetic Analysis," *Trends in Genetics*, 1:22–25 (1985).

Wenke et al.,"A Study of Betel Quid Carcinogenesis. II. Formation of N–Nitrosamines During Betel Quid Chewing," N–Nitroso Compounds: Occurrence, Biological Effects and Relevance to Human Cancer, Proceedings of the VIIIth International Symposium on N–Nitroso Compounds held in Banff, Canada, Sep. 5–9, 1983, IARC Scientific Publications No. 57, pp. 859–866.

West et al., "Duplex–Duplex Interactions Catalyzed by RecA protein Allow Strand Exchanges to Pass Double–Strand Breaks in DNA," *Cell*, 37:683–691 (1984).

Wiemik et al., "Effect of Air–Curing on the Chemical Composition of Tobacco," *Recent Advances in Tobacco Science*, vol. 21, pp. 39–80, et. Seq., Symposium Proceedings $49^{th}$ Meeting Tobacco Chemists' Research Conference, Sep. 24–27, 1995, Lexington, Kentucky.

Zaridze et al., "The Effect of Nass Use and Smoking on the Risk of Oral Leukoplakia," *Cancer Detection and Prevention*, 9:435–440 (1986).

International Search Report—date of mailing Oct. 22, 1998.

* cited by examiner

```
caaaaactat tttccacaaa attcatttca caaccccccc aaaaaaaaac cATGTTTAGA   60
GCTATTCCTT TCACTGCTAC AGTGCATCCT TATGCAATTA CAGCTCCAAG GTTGGTGGTG  120
AAAATGTCAG CAATAGCCAC CAAGAATACA AGAGTGGAGT CATTAGAGGT GAAACCACCA  180
GCACACCCAA CTTATGATTT AAAGGAAGTT ATGAAACTTG CACTCTCTGA AGATGCTGGG  240
TTTCTAGCAA AGGAAGACGG GATCATAGCA GGAATTGCAC TTGCTGAGAT GATATTCGCG  360
GAAGTTGATC CTTCATTAAA GGTGGAGTGG TATGTAAATG ATGGCGATAA AGTTCATAAA  420
GGCTTGAAAT TTGGCAAAGT ACAAGGAAAC GCTTACAACA TTGTTATAGC TGAGAGGGTT  480
GTTCTCAATT TTATGCAAAG AATGAGTGGA ATAGCTACAC TAACTAAGGA AATGGCAGAT  540
GCTGCACACC CTGCTTACAT CTTGGAGACT AGGAAAACTG CTCCTGGATT ACGTTTGGTG  600
GATAAATGGG CGGTATTGAT CGGTGGGGGG AAGAATCACA GAATGGGCTT ATTTGATATG  660
GTAATGATAA AAGACAATCA CATATCTGCT GCTGGAGGTG TCGGCAAAGC TCTAAAATCT  720
GTGGATCAGT ATTTGGAGCA AAATAAACTT CAAATAGGGG TTGAGGTTGA AACCAGGACA  780
ATTGAAGAAG TACGTGAGGT TCTAGACTAT GCATCTCAAA CAAAGACTTC GTTGACTAGG  840
ATAATGCTGG ACAATATGGT TGTTCCATTA TCTAACGGAG ATATTGATGT ATCCATGCTT  900
AAGGAGGCTG TAGAATTGAT CAATGGGAGG TTTGATACGG AGGCTTCAGG AAATGTTACC  960
CTTGAAACAG TACACAAGAT TGGACAAACT GGTGTTACCT ACATTTCTAG TGGTGCCCTG 1020
ACGCATTCCG TGAAAGCACT TGACATTTCC CTGAAGATCG ATACAGAGCT CGCCCTTGAA 1080
GTTGGAAGGC GTACAAAACG AGCATGAgcg ccattacttc tgctataggg ttggagtaaa 1140
agcagctgaa tagctgaaag gtgcaaataa gaatcatttt actagttgtc aaacaaaaga 1200
tccttcactg tgtaatcaaa caaaagatg taaattgctg gaatatctca gatggctctt 1260
ttccaacctt attgcttgag ttggtaattt cattatagct ttgttttcat gtttcatgga 1320
atttgttaca atgaaaatac ttgatttata agtttggtgt atgtaaaatt ctgtgttact 1380
tcaaatattt tgagatgtt                                              1399
                SEQ ID NO:1 (SEQ ID NO:3 all caps)
                         FIGURE 2A
```

```
MFRAIPFTAT VHPYAITAPR LVVKMSAIAT KNTRVESLEV KPPAHPTYDL   50
KEVMKLALSE DAGNLGDVTC KATIPLDMES DAHFLAKEDG IIAGIALAEM  100
IFAEVDPSLK VEWYVNDGDK VHKGLKFGKV QGNAYNIVIA ERVVLNFMQR  150
MSGIATLTKE MADAAHPAYI LETRKTAPGL RLVDKWAVLI GGGKNHRMGL  200
FDMVMIKDNH ISAAGGVGKA LKSVDQYLEQ NKLQIGVEVE TRTIEEVREV  250
LDYASQTKTS LTRIMLDNMV VPLSNGDIDV SMLKEAVELI NGRFDTEASG  300
NVTLETVHKI GQTGVTYISS GALTHSVKAL DISLKIDTEL ALEVGRRTKR  350
A                                                      351
                    SEQ ID NO:2
                    FIGURE 2B
```

```
N. tabacum      MFRAIPFTATVHPYAITAPRLVVKMSAIATKNTRVESLEVKPPAHPTYDL  SEQ ID NO. 4
R. rubrum       *--------RPNH-----------------------PVAALS*F----AI  SEQ ID NO. 5
M. leprae       *--------LSDC-----------------------EFDAAR--------  SEQ ID NO:6
S. typhimurium  *--------PPRR*NPDDR*-----------DALL*RINLDI*A----AV  SEQ ID NO:7
E. coli         *--------PPRR*NPDTR*-----------DELL*RINLDI*G----AV  SEQ ID NO:8
H. sapien       *---------------D*EG*ALLLPPVTLAALVDSWLREDC*G------  SEQ ID NO:9
S. cerevisiae   *---------------PVYE-HLLPVNGAWRQDVTNWLSEDV*S------  SEQ ID NO:10

N. tabacum      KEVMKLALSEDAGNLGDVTCKATIPLDMESDAHFLAKEDGIIAGIA----  SEQ ID NO: 11
R. rubrum       D*AVRR**A**L*RA**I*ST****AATRAH*RFV*RQP**L**LGCA--  SEQ ID NO:12
M. leprae       -DTIRR**H**LRYGL*I*TQ**V*AGTVVTGSMVPR*P*VIAGVDVALL  SEQ ID NO:13
S. typhimurium  AQALREDLGGEVDAGN*I*AQL-L*A*TQAH*TVITR*D*VF----CGKR  SEQ ID NO:14
E. coli         AQALREDLGGTVDANN*I*A*L-L*ENSR*H*TVITR*N*VF----CGKR  SEQ ID NO:15
H. sapien       -----------------LNYAALVSGAGP*QAALWAKSP*VL----AGQP  SEQ ID NO:16
S. cerevisiae   -----------------FDFGGYVVGSDLKEANLYCKQD*ML----CGVP  SEQ ID NO:17

N. tabacum      -LAEMIFAEVDPSLKVEWYVNDGDKVHKGLK------FGKVQGNAYNIVI  SEQ ID NO:18
R. rubrum       --RSAF-ALLDDTVTFTTPLE**AEIAA*QT------VAE*A*A*RT*LA  SEQ ID NO:19
M. leprae       VLD*VF-GVDGYRVLY--R*E**ARLQS*QP------LLTVQAA*RGLLT  SEQ ID NO:20
S. typhimurium  WVE*VFIQLAGDDVRLT*H*D***AI*ANQT------VFELN*PARVLLT  SEQ ID NO:21
E. coli         WVE*VFIQLAGDDVTII*H*D***VINANQS------LFELE*PSRVLLT  SEQ ID NO:22
H. sapien       FFDAIFTQL---NCQVS*FLPE*S*LVPVAR------VAEVR*P*HDLLL  SEQ ID NO:23
S. cerevisiae   FAW*VFNQC---ELQVE*LFKE*SFLEPSKNDSGKIVVAKIT*P*K**LL  SEQ ID NO:24

N. tabacum      AERVVLNFMQRMSGIATLTKEMAD--AAH--PAYILETRKTAPGLRLVDK  SEQ ID NO:25
R. rubrum       ***TA***LGHL*****R*RRFG*AI*HT--R*RLTC****T****GLE*  SEQ ID NO:26
M. leprae       ***TM***VCHM*****V*VAWV*AVRGT--K*KIRD****L****ALQ*  SEQ ID NO:27
S. typhimurium  G**TA***V*TL**VASEVRRYVGLL*GT--QTQL*D****L****TAL*  SEQ ID NO:28
E. coli         G*PTA***V*TL**VASKVRHYVELLEGT--NTQL*D****L****SAL*  SEQ ID NO:29
H. sapien       G***A**TLARC****SAAAAAVEAARGAGWTGHVAG****T**F***E*  SEQ ID NO:30
S. cerevisiae   ***TA**ILSRS****TASHKIISLARSTGYKGTIAG****T****RLE*  SEQ ID NO:31

N. tabacum      WAVLIGGGKNHRMGLFDMVMIKDNHISAAGGVGKALKSVDQYLEQNKLQI  SEQ ID NO: 32
R. rubrum       Y**RC***S***F**D*A*L******AVA***SA**SRAR-AGVGHMVRI  SEQ ID NO:33
M. leprae       Y**RV***V***L**G*TAL*****VA*V*S*VD**RA*R-AAAPEL-PC  SEQ ID NO:34
S. typhimurium  Y***C***A***L**T*AFL******I*S*S*RQ*VEKAF-W*HPD-APV  SEQ ID NO:35
E. coli         Y***C***A***L**S*AFL******I*S*S*RQ*VEKAS-W*HPD-APV  SEQ ID NO:36
H. sapien       YGL*V**AAS**YD*GGLVML*D**VVPP***EK*VRAARQ---AADFAL  SEQ ID NO:37
S. cerevisiae   YSM*V**CDT**YD*SS**ML*D***W*T*SITN*V*NARA---VCGFAV  SEQ ID NO:38
```

FIGURE 3

| | | |
|---|---|---|
| N. tabacum | GVEVETRTIEEVREVLDYASQTKTSLTRIMLDNMVVPLSNGDIDVSMLKE | SEQ ID NO: 39 |
| R. rubrum | EI****--L*QLA***AVGGAEV-----VL****-----DAPT----*TR | SEQ ID NO: 40 |
| M. leprae | E****S--L*QLDAM*A-EEPEL-----*L***F--*VWQTQV----AVQ | SEQ ID NO: 41 |
| S. typhimurium | E****N--LDELDDA*K-*GADI-----*****F-----NTDQ----MR* | SEQ ID NO: 42 |
| E. coli | E****N--L**LD*A*K-*GADI-----*****F-----ETEQ----MR* | SEQ ID NO: 43 |
| H. sapien | K****CSSLQ**VQAAE-*GADL-----VL***F------KPEELHPTAT | SEQ ID NO: 44 |
| S. cerevisiae | KI***CLSED*AT*AIE-*GADV-----*****F------KGDGLK*CAQ | SEQ ID NO: 45 |

| | | |
|---|---|---|
| N. tabacum | AVELI---NGRFDTEASGNVTLETVHKIG-QTGVTYISSGALTHSVKALD | SEQ ID NO: 46 |
| R. rubrum | **DMV---A**LV*****G*S*D*IAALA-ES**D***V*******TT** | SEQ ID NO: 47 |
| M. leprae | RRDIR---APTVLL*S**GLS**NAAIYA-G***DYLAV*******RI** | SEQ ID NO: 48 |
| S. typhimurium | **KRV---**QARL*V*****AE*LREFA-E***DF**VG******R*** | SEQ ID NO: 49 |
| E. coli | **KRT---**KALL*V*****DK*LREFA-E***DF**V*******Q*** | SEQ ID NO: 50 |
| H. sapien | *LKAQFPSVA---VEA**GIT*DNLPQF-CGPHIDV**M*M**QA*P*** | SEQ ID NO: 51 |
| S. cerevisiae | SLKNKWNGKKHFLLEC**GLN*DNLEEYLCD-DIDIY*TSSIHQGTPVI* | SEQ ID NO: 52 |

| | | % Identity | % Similarity | |
|---|---|---|---|---|
| N. tabacum | ISKLIDTELALEVGRRTKRA | | | SEQ ID NO: 53 |
| R. rubrum | *G*D*VVA-----PPKAERA | 15.9 | 43.2 | SEQ ID NO: 54 |
| M. leprae | *G*DL | 18.3 | 37.3 | |
| S. typhimurium | LSMRFC | 18.2 | 34.8 | SEQ ID NO: 55 |
| E. coli | LSMRFR | 17.9 | 32.8 | SEQ ID NO: 56 |
| H. sapien | F***L---F*K*VAPVP*IH | 16.8 | 31.7 | SEQ ID NO: 57 |
| S. cerevisiae | F***LAH | 14.6 | 27.8 | SEQ ID NO: 58 |

FIGURE 3 continued

SEQUENCE LISTING

<160> NUMBER OF SEQ ID NOS: 58

<210> SEQ ID NO 1
<211> LENGTH: 1399
<212> TYPE: DNA
<213> ORGANISM: Nicotiana tabacum

<400> SEQUENCE: 1

```
caaaaactat tttccacaaa attcatttca caaccccccc aaaaaaaaac catgtttaga     60

gctattcctt tcactgctac agtgcatcct tatgcaatta cagctccaag gttggtggtg    120

aaaatgtcag caatagccac caagaataca agagtggagt cattagaggt gaaaccacca    180

gcacacccaa cttatgattt aaaggaagtt atgaaacttg cactctctga agatgctggg    240

aatttaggag atgtgacttg taaggcgaca attcctcttg atatggaatc cgatgctcat    300

tttctagcaa aggaagacgg gatcatagca ggaattgcac ttgctgagat gatattcgcg    360

gaagttgatc cttcattaaa ggtggagtgg tatgtaaatg atggcgataa agttcataaa    420

ggcttgaaat ttggcaaagt acaaggaaac gcttacaaca ttgttatagc tgagagggtt    480

gttctcaatt ttatgcaaag aatgagtgga atagctacac taactaagga aatggcagat    540

gctgcacacc ctgcttacat cttggagact aggaaaactg ctcctggatt acgtttggtg    600

gataaatggg cggtattgat cggtgggggg aagaatcaca gaatgggctt atttgatatg    660
```

-continued gtaatgataa aagacaatca catatctgct gctggaggtg tcggcaaagc tctaaaatct 720
gtggatcagt atttggagca aaataaactt caaatagggg ttgaggttga aaccaggaca 780
attgaagaag tacgtgaggt tctagactat gcatctcaaa caaagacttc gttgactagg 840
ataatgctgg acaatatggt tgttccatta tctaacggag atattgatgt atccatgctt 900
aaggaggctg tagaattgat caatgggagg tttgatacgg aggcttcagg aaatgttacc 960
cttgaaacag tacacaagat tggacaaact ggtgttacct acatttctag tggtgccctg 1020
acgcattccg tgaaagcact tgacatttcc ctgaagatcg atacagagct cgcccttgaa 1080
gttggaaggc gtacaaaacg agcatgagcg ccattacttc tgctataggg ttggagtaaa 1140
agcagctgaa tagctgaaag gtgcaaataa gaatcatttt actagttgtc aaacaaaaga 1200
tccttcactg tgtaatcaaa caaaaagatg taaattgctg gaatatctca gatggctctt 1260
ttccaacctt attgcttgag ttggtaattt cattatagct ttgttttcat gtttcatgga 1320
atttgttaca atgaaaatac ttgatttata agtttggtgt atgtaaaatt ctgtgttact 1380
tcaaatattt tgagatgtt 1399

<210> SEQ ID NO 2
<211> LENGTH: 351
<212> TYPE: PRT
<213> ORGANISM: Nicotiana tabacum

<400> SEQUENCE: 2

Met Phe Arg Ala Ile Pro Phe Thr Ala Thr Val His Pro Tyr Ala Ile
1 5 10 15

Thr Ala Pro Arg Leu Val Val Lys Met Ser Ala Ile Ala Thr Lys Asn
20 25 30

Thr Arg Val Glu Ser Leu Glu Val Lys Pro Pro Ala His Pro Thr Tyr
35 40 45

Asp Leu Lys Glu Val Met Lys Leu Ala Leu Ser Glu Asp Ala Gly Asn
50 55 60

Leu Gly Asp Val Thr Cys Lys Ala Thr Ile Pro Leu Asp Met Glu Ser
65 70 75 80

Asp Ala His Phe Leu Ala Lys Glu Asp Gly Ile Ile Ala Gly Ile Ala
85 90 95

Leu Ala Glu Met Ile Phe Ala Glu Val Asp Pro Ser Leu Lys Val Glu
100 105 110

Trp Tyr Val Asn Asp Gly Asp Lys Val His Lys Gly Leu Lys Phe Gly
115 120 125

Lys Val Gln Gly Asn Ala Tyr Asn Ile Val Ile Ala Glu Arg Val Val
130 135 140

Leu Asn Phe Met Gln Arg Met Ser Gly Ile Ala Thr Leu Thr Lys Glu
145 150 155 160

Met Ala Asp Ala Ala His Pro Ala Tyr Ile Leu Glu Thr Arg Lys Thr
165 170 175

Ala Pro Gly Leu Arg Leu Val Asp Lys Trp Ala Val Leu Ile Gly Gly
180 185 190

Gly Lys Asn His Arg Met Gly Leu Phe Asp Met Val Met Ile Lys Asp
195 200 205

Asn His Ile Ser Ala Ala Gly Gly Val Gly Lys Ala Leu Lys Ser Val
210 215 220

Asp Gln Tyr Leu Glu Gln Asn Lys Leu Gln Ile Gly Val Glu Val Glu
225 230 235 240

-continued

```
Thr Arg Thr Ile Glu Glu Val Arg Glu Val Leu Asp Tyr Ala Ser Gln
                245                 250                 255

Thr Lys Thr Ser Leu Thr Arg Ile Met Leu Asp Asn Met Val Val Pro
            260                 265                 270

Leu Ser Asn Gly Asp Ile Asp Val Ser Met Leu Lys Glu Ala Val Glu
        275                 280                 285

Leu Ile Asn Gly Arg Phe Asp Thr Glu Ala Ser Gly Asn Val Thr Leu
    290                 295                 300

Glu Thr Val His Lys Ile Gly Gln Thr Gly Val Thr Tyr Ile Ser Ser
305                 310                 315                 320

Gly Ala Leu Thr His Ser Val Lys Ala Leu Asp Ile Ser Leu Lys Ile
                325                 330                 335

Asp Thr Glu Leu Ala Leu Glu Val Gly Arg Arg Thr Lys Arg Ala
            340                 345                 350


<210> SEQ ID NO 3
<211> LENGTH: 1053
<212> TYPE: DNA
<213> ORGANISM: Nicotiana tabacum

<400> SEQUENCE: 3

atgtttagag ctattccttt cactgctaca gtgcatcctt atgcaattac agctccaagg      60

ttggtggtga aaatgtcagc aatagccacc aagaatacaa gagtggagtc attagaggtg     120

aaaccaccag cacacccaac ttatgattta aaggaagtta tgaaacttgc actctctgaa     180

gatgctggga atttaggaga tgtgacttgt aaggcgacaa ttcctcttga tatggaatcc     240

gatgctcatt ttctagcaaa ggaagacggg atcatagcag gaattgcact tgctgagatg     300

atattcgcgg aagttgatcc ttcattaaag gtggagtggt atgtaaatga tggcgataaa     360

gttcataaag gcttgaaatt tggcaaagta caaggaaacg cttacaacat tgttatagct     420

gagagggttg ttctcaattt tatgcaaaga atgagtggaa tagctacact aactaaggaa     480

atggcagatg ctgcacaccc tgcttacatg ttggagacta ggaaaactgc tcctggatta     540

cgtttggtgg ataaatgggc ggtattgatc ggtgggggga agaatcacag aatgggctta     600

tttgatatgg taatgataaa agacaatcac atatctgctg ctggaggtgt cggcaaagct     660

ctaaaatctg tggatcagta tttggagcaa aataaacttc aaataggggt tgaggttgaa     720

accaggacaa ttgaagaagt acgtgaggtt ctagactatg catctcaaac aaagacttcg     780

ttgactagga taatgctgga caatatggtt gttccattat ctaacggaga tattgatgta     840

tccatgctta aggaggctgt agaattgatc aatgggaggt ttgatacgga ggcttcagga     900

aatgttaccc ttgaaacagt acacaagatt ggacaaactg gtgttaccta catttctagt     960

ggtgccctga cgcattccgt gaaagcactt gacatttccc tgaagatcga tacagagctc    1020

gcccttgaag ttggaaggcg tacaaaacga gca                                1053


<210> SEQ ID NO 4
<211> LENGTH: 50
<212> TYPE: PRT
<213> ORGANISM: Nicotiana tabacum

<400> SEQUENCE: 4

Met Phe Arg Ala Ile Pro Phe Thr Ala Thr Val His Pro Tyr Ala Ile
 1               5                  10                  15

Thr Ala Pro Arg Leu Val Val Lys Met Ser Ala Ile Ala Thr Lys Asn
            20                  25                  30
```

-continued

```
Thr Arg Val Glu Ser Leu Glu Val Lys Pro Pro Ala His Pro Thr Tyr
        35                  40                  45

Asp Leu
    50


<210> SEQ ID NO 5
<211> LENGTH: 13
<212> TYPE: PRT
<213> ORGANISM: Rhodospirillum rubrum

<400> SEQUENCE: 5

Arg Pro Asn His Pro Val Ala Ala Leu Ser Phe Ala Ile
 1               5                  10


<210> SEQ ID NO 6
<211> LENGTH: 10
<212> TYPE: PRT
<213> ORGANISM: Mycobacterium lepre

<400> SEQUENCE: 6

Leu Ser Asp Cys Glu Phe Asp Ala Ala Arg
 1               5                  10


<210> SEQ ID NO 7
<211> LENGTH: 22
<212> TYPE: PRT
<213> ORGANISM: Salmonella typhimurium

<400> SEQUENCE: 7

Pro Pro Arg Arg Asn Pro Asp Asp Arg Asp Ala Leu Leu Arg Ile Asn
 1               5                  10                  15

Leu Asp Ile Ala Ala Val
            20


<210> SEQ ID NO 8
<211> LENGTH: 22
<212> TYPE: PRT
<213> ORGANISM: Escherichia coli

<400> SEQUENCE: 8

Pro Pro Arg Arg Asn Pro Asp Thr Arg Asp Glu Leu Leu Arg Ile Asn
 1               5                  10                  15

Leu Asp Ile Gly Ala Val
            20


<210> SEQ ID NO 9
<211> LENGTH: 25
<212> TYPE: PRT
<213> ORGANISM: Homo sapiens

<400> SEQUENCE: 9

Asp Glu Gly Ala Leu Leu Leu Pro Pro Val Thr Leu Ala Ala Leu Val
 1               5                  10                  15

Asp Ser Trp Leu Arg Glu Asp Cys Gly
            20                  25


<210> SEQ ID NO 10
<211> LENGTH: 26
<212> TYPE: PRT
<213> ORGANISM: Saccharomyces cerevisiae

<400> SEQUENCE: 10

Pro Val Tyr Glu His Leu Leu Pro Val Asn Gly Ala Trp Arg Gln Asp
```

-continued

```
 1               5                   10                  15

Val Thr Asn Trp Leu Ser Glu Asp Val Ser
            20                  25


<210> SEQ ID NO 11
<211> LENGTH: 46
<212> TYPE: PRT
<213> ORGANISM: Nicotiana tabacum

<400> SEQUENCE: 11

Lys Glu Val Met Lys Leu Ala Leu Ser Glu Asp Ala Gly Asn Leu Gly
 1               5                   10                  15

Asp Val Thr Cys Lys Ala Thr Ile Pro Leu Asp Met Glu Ser Asp Ala
            20                  25                  30

His Phe Leu Ala Lys Glu Asp Gly Ile Ile Ala Gly Ile Ala
        35                  40                  45


<210> SEQ ID NO 12
<211> LENGTH: 29
<212> TYPE: PRT
<213> ORGANISM: Rhodospirillum rubrum

<400> SEQUENCE: 12

Asp Ala Val Arg Arg Ala Leu Arg Ala Ile Ser Thr Ala Ala Thr Arg
 1               5                   10                  15

Ala His Arg Phe Val Arg Gln Pro Leu Leu Gly Cys Ala
            20                  25


<210> SEQ ID NO 13
<211> LENGTH: 38
<212> TYPE: PRT
<213> ORGANISM: Mycobacterium lepre

<400> SEQUENCE: 13

Asp Thr Ile Arg Arg His Leu Arg Tyr Gly Leu Ile Thr Gln Val Ala
 1               5                   10                  15

Gly Thr Val Val Thr Gly Ser Met Val Pro Arg Pro Val Ile Ala Gly
            20                  25                  30

Val Asp Val Ala Leu Leu
        35


<210> SEQ ID NO 14
<211> LENGTH: 38
<212> TYPE: PRT
<213> ORGANISM: Nicotiana tabacum

<400> SEQUENCE: 14

Ala Gln Ala Leu Arg Glu Asp Leu Gly Gly Glu Val Asp Ala Gly Asn
 1               5                   10                  15

Ile Ala Gln Leu Leu Ala Thr Gln Ala His Thr Val Ile Thr Arg Asp
            20                  25                  30

Val Phe Cys Gly Lys Arg
        35


<210> SEQ ID NO 15
<211> LENGTH: 37
<212> TYPE: PRT
<213> ORGANISM: Salmonella typhimurium

<400> SEQUENCE: 15

Ala Gln Ala Leu Arg Glu Asp Leu Gly Gly Thr Val Asp Ala Asn Asn
```

-continued

```
1               5                   10                  15

Ile Ala Leu Leu Glu Asn Ser Arg His Thr Val Ile Thr Arg Asn Val
            20                  25                  30

Phe Cys Gly Lys Arg
        35


<210> SEQ ID NO 16
<211> LENGTH: 27
<212> TYPE: PRT
<213> ORGANISM: Homo sapiens

<400> SEQUENCE: 16

Leu Asn Tyr Ala Ala Leu Val Ser Gly Ala Gly Pro Gln Ala Ala Leu
 1               5                  10                  15

Trp Ala Lys Ser Pro Val Leu Ala Gly Gln Pro
            20                  25


<210> SEQ ID NO 17
<211> LENGTH: 28
<212> TYPE: PRT
<213> ORGANISM: Sacharomyces cerevisiae

<400> SEQUENCE: 17

Phe Asp Phe Gly Gly Tyr Val Val Gly Ser Asp Leu Lys Glu Ala Asn
 1               5                  10                  15

Leu Tyr Cys Lys Gln Asp Met Leu Cys Gly Val Pro
            20                  25


<210> SEQ ID NO 18
<211> LENGTH: 43
<212> TYPE: PRT
<213> ORGANISM: Nicotiana tabacum

<400> SEQUENCE: 18

Leu Ala Glu Met Ile Phe Ala Glu Val Asp Pro Ser Leu Lys Val Glu
 1               5                  10                  15

Trp Tyr Val Asn Asp Gly Asp Lys Val His Lys Gly Leu Lys Phe Gly
            20                  25                  30

Lys Val Gln Gly Asn Ala Tyr Asn Ile Val Ile
        35                  40


<210> SEQ ID NO 19
<211> LENGTH: 34
<212> TYPE: PRT
<213> ORGANISM: Rhodospirillum rubrum

<400> SEQUENCE: 19

Arg Ser Ala Phe Ala Leu Leu Asp Asp Thr Val Thr Phe Thr Thr Pro
 1               5                  10                  15

Leu Glu Ala Glu Ile Ala Ala Gln Thr Val Ala Glu Ala Ala Arg Thr
            20                  25                  30

Leu Ala


<210> SEQ ID NO 20
<211> LENGTH: 35
<212> TYPE: PRT
<213> ORGANISM: Mycobacterium lepre

<400> SEQUENCE: 20

Val Leu Asp Val Phe Gly Val Asp Gly Tyr Arg Val Leu Tyr Arg Glu
 1               5                  10                  15
```

-continued

```
Ala Arg Leu Gln Ser Gln Pro Leu Leu Thr Val Gln Ala Ala Arg Gly
            20                  25                  30

Leu Leu Thr
        35


<210> SEQ ID NO 21
<211> LENGTH: 36
<212> TYPE: PRT
<213> ORGANISM: Salmonella typhimurium

<400> SEQUENCE: 21

Trp Val Glu Val Phe Ile Gln Leu Ala Gly Asp Asp Val Arg Leu Thr
 1               5                  10                  15

His Asp Ala Ile Ala Asn Gln Thr Val Phe Glu Leu Asn Pro Ala Arg
            20                  25                  30

Val Leu Leu Thr
        35


<210> SEQ ID NO 22
<211> LENGTH: 37
<212> TYPE: PRT
<213> ORGANISM: Escherichia coli

<400> SEQUENCE: 22

Trp Val Glu Val Phe Ile Gln Leu Ala Gly Asp Asp Val Thr Ile Ile
 1               5                  10                  15

His Asp Val Ile Asn Ala Asn Gln Ser Leu Phe Glu Leu Glu Pro Ser
            20                  25                  30

Arg Val Leu Leu Thr
        35


<210> SEQ ID NO 23
<211> LENGTH: 36
<212> TYPE: PRT
<213> ORGANISM: Homo sapiens

<400> SEQUENCE: 23

Phe Phe Asp Ala Ile Phe Thr Gln Leu Asn Cys Gln Val Ser Phe Leu
 1               5                  10                  15

Pro Glu Ser Leu Val Pro Val Ala Arg Val Ala Glu Val Arg Pro His
            20                  25                  30

Asp Leu Leu Leu
        35


<210> SEQ ID NO 24
<211> LENGTH: 40
<212> TYPE: PRT
<213> ORGANISM: Saccharomyces cerevisiae

<400> SEQUENCE: 24

Phe Ala Trp Val Phe Asn Gln Cys Glu Leu Gln Val Glu Leu Phe Lys
 1               5                  10                  15

Glu Ser Phe Leu Glu Pro Ser Lys Asn Asp Ser Gly Lys Ile Val Val
            20                  25                  30

Ala Lys Ile Thr Pro Lys Leu Leu
        35                  40


<210> SEQ ID NO 25
<211> LENGTH: 46
<212> TYPE: PRT
```

-continued

```
<213> ORGANISM: Nicotiana tabacum

<400> SEQUENCE: 25

Ala Glu Arg Val Val Leu Asn Phe Met Gln Arg Met Ser Gly Ile Ala
 1               5                  10                  15

Thr Leu Thr Lys Glu Met Ala Asp Ala Ala His Pro Ala Tyr Ile Leu
            20                  25                  30

Glu Thr Arg Lys Thr Ala Pro Gly Leu Arg Leu Val Asp Lys
        35                  40                  45


<210> SEQ ID NO 26
<211> LENGTH: 24
<212> TYPE: PRT
<213> ORGANISM: Rhodospirillum rubrum

<400> SEQUENCE: 26

Thr Ala Leu Gly His Leu Arg Arg Arg Phe Gly Ala Ile His Thr Arg
 1               5                  10                  15

Arg Leu Thr Cys Thr Gly Leu Glu
            20


<210> SEQ ID NO 27
<211> LENGTH: 25
<212> TYPE: PRT
<213> ORGANISM: Mycobacterium lepre

<400> SEQUENCE: 27

Thr Met Val Cys His Met Val Val Ala Trp Val Ala Val Arg Gly Thr
 1               5                  10                  15

Lys Lys Ile Arg Asp Leu Ala Leu Gln
            20                  25


<210> SEQ ID NO 28
<211> LENGTH: 29
<212> TYPE: PRT
<213> ORGANISM: Salmonella typhimurium

<400> SEQUENCE: 28

Gly Thr Ala Val Thr Leu Val Ala Ser Glu Val Arg Arg Tyr Val Gly
 1               5                  10                  15

Leu Leu Gly Thr Gln Thr Gln Leu Asp Leu Thr Ala Leu
            20                  25


<210> SEQ ID NO 29
<211> LENGTH: 31
<212> TYPE: PRT
<213> ORGANISM: Escherichia coli

<400> SEQUENCE: 29

Gly Pro Thr Ala Val Thr Leu Val Ala Ser Lys Val Arg His Tyr Val
 1               5                  10                  15

Glu Leu Leu Glu Gly Thr Asn Thr Gln Leu Asp Leu Ser Ala Leu
            20                  25                  30


<210> SEQ ID NO 30
<211> LENGTH: 31
<212> TYPE: PRT
<213> ORGANISM: Homo sapiens

<400> SEQUENCE: 30

Gly Ala Thr Leu Ala Arg Cys Ser Ala Ala Ala Ala Ala Val Glu Ala
 1               5                  10                  15
```

-continued

```
Ala Arg Gly Ala Gly Trp Thr Gly His Val Ala Gly Thr Phe Glu
            20                  25                  30


<210> SEQ ID NO 31
<211> LENGTH: 32
<212> TYPE: PRT
<213> ORGANISM: Saccharomyces cerevisiae

<400> SEQUENCE: 31

Thr Ala Ile Leu Ser Arg Ser Thr Ala Ser His Lys Ile Ile Ser Leu
 1               5                  10                  15

Ala Arg Ser Thr Gly Tyr Lys Gly Thr Ile Ala Gly Thr Arg Leu Glu
            20                  25                  30


<210> SEQ ID NO 32
<211> LENGTH: 50
<212> TYPE: PRT
<213> ORGANISM: Nicotiana tabacum

<400> SEQUENCE: 32

Trp Ala Val Leu Ile Gly Gly Gly Lys Asn His Arg Met Gly Leu Phe
 1               5                  10                  15

Asp Met Val Met Ile Lys Asp Asn His Ile Ser Ala Ala Gly Gly Val
            20                  25                  30

Gly Lys Ala Leu Lys Ser Val Asp Gln Tyr Leu Glu Gln Asn Lys Leu
        35                  40                  45

Gln Ile
    50


<210> SEQ ID NO 33
<211> LENGTH: 26
<212> TYPE: PRT
<213> ORGANISM: Rhodospirillum rubrum

<400> SEQUENCE: 33

Tyr Arg Cys Ser Phe Asp Ala Leu Ala Val Ala Ser Ala Ser Arg Ala
 1               5                  10                  15

Arg Ala Gly Val Gly His Met Val Arg Ile
            20                  25


<210> SEQ ID NO 34
<211> LENGTH: 26
<212> TYPE: PRT
<213> ORGANISM: Mycobacterium lepre

<400> SEQUENCE: 34

Tyr Arg Val Val Leu Gly Thr Ala Leu Val Ala Val Ser Val Asp Arg
 1               5                  10                  15

Ala Arg Ala Ala Ala Pro Glu Leu Pro Cys
            20                  25


<210> SEQ ID NO 35
<211> LENGTH: 25
<212> TYPE: PRT
<213> ORGANISM: Salmonella typhimurium

<400> SEQUENCE: 35

Tyr Cys Ala Leu Thr Ala Phe Leu Ile Ser Ser Arg Gln Val Glu Lys
 1               5                  10                  15

Ala Phe Trp His Pro Asp Ala Pro Val
            20                  25
```

-continued

<210> SEQ ID NO 36
<211> LENGTH: 25
<212> TYPE: PRT
<213> ORGANISM: Escherichia coli

<400> SEQUENCE: 36

```
Tyr Cys Ala Leu Ser Ala Phe Leu Ile Ser Ser Arg Gln Val Glu Lys
 1               5                  10                  15

Ala Ser Trp His Pro Asp Ala Pro Val
            20                  25
```

<210> SEQ ID NO 37
<211> LENGTH: 34
<212> TYPE: PRT
<213> ORGANISM: Homo sapiens

<400> SEQUENCE: 37

```
Tyr Gly Leu Val Ala Ala Ser Tyr Asp Gly Gly Leu Val Met Leu Asp
 1               5                  10                  15

Val Val Pro Pro Phe Lys Val Arg Ala Ala Arg Gln Ala Ala Asp Phe
            20                  25                  30

Ala Leu
```

<210> SEQ ID NO 38
<211> LENGTH: 31
<212> TYPE: PRT
<213> ORGANISM: Saccharomyces cerevisiae

<400> SEQUENCE: 38

```
Tyr Ser Met Val Cys Asp Thr Tyr Asp Ser Ser Met Leu Asp Trp Thr
 1               5                  10                  15

Ser Ile Thr Asn Val Asn Ala Arg Ala Val Cys Gly Phe Ala Val
            20                  25                  30
```

<210> SEQ ID NO 39
<211> LENGTH: 50
<212> TYPE: PRT
<213> ORGANISM: Nicotiana tabacum

<400> SEQUENCE: 39

```
Gly Val Glu Val Glu Thr Arg Thr Ile Glu Glu Val Arg Glu Val Leu
 1               5                  10                  15

Asp Tyr Ala Ser Gln Thr Lys Thr Ser Leu Thr Arg Ile Met Leu Asp
            20                  25                  30

Asn Met Val Val Pro Leu Ser Asn Gly Asp Ile Asp Val Ser Met Leu
        35                  40                  45

Lys Glu
    50
```

<210> SEQ ID NO 40
<211> LENGTH: 21
<212> TYPE: PRT
<213> ORGANISM: Rhodospirillum rubrum

<400> SEQUENCE: 40

```
Glu Ile Leu Gln Leu Ala Ala Val Gly Gly Ala Glu Val Val Leu Asp
 1               5                  10                  15

Ala Pro Thr Thr Arg
            20
```

-continued

<210> SEQ ID NO 41
<211> LENGTH: 25
<212> TYPE: PRT
<213> ORGANISM: Mycobacterium lepre

<400> SEQUENCE: 41

Glu Ser Leu Gln Leu Asp Ala Met Ala Glu Glu Pro Glu Leu Leu Phe
1 5 10 15

Val Trp Gln Thr Gln Val Ala Val Gln
20 25

<210> SEQ ID NO 42
<211> LENGTH: 21
<212> TYPE: PRT
<213> ORGANISM: Salmonella typhimurium

<400> SEQUENCE: 42

Glu Asn Leu Asp Glu Leu Asp Asp Ala Lys Gly Ala Asp Ile Phe Asn
1 5 10 15

Thr Asp Gln Met Arg
20

<210> SEQ ID NO 43
<211> LENGTH: 18
<212> TYPE: PRT
<213> ORGANISM: Escherichia coli

<400> SEQUENCE: 43

Glu Asn Leu Leu Asp Ala Lys Gly Ala Asp Ile Phe Glu Thr Glu Gln
1 5 10 15

Met Arg

<210> SEQ ID NO 44
<211> LENGTH: 28
<212> TYPE: PRT
<213> ORGANISM: Homo sapiens

<400> SEQUENCE: 44

Lys Cys Ser Ser Leu Gln Val Gln Ala Ala Glu Gly Ala Asp Leu Val
1 5 10 15

Leu Phe Lys Pro Glu Glu Leu His Pro Thr Ala Thr
20 25

<210> SEQ ID NO 45
<211> LENGTH: 26
<212> TYPE: PRT
<213> ORGANISM: Saccharomyces cerevisiae

<400> SEQUENCE: 45

Lys Ile Cys Leu Ser Glu Asp Ala Thr Ala Ile Glu Gly Ala Asp Val
1 5 10 15

Phe Lys Gly Asp Gly Leu Lys Cys Ala Gln
20 25

<210> SEQ ID NO 46
<211> LENGTH: 46
<212> TYPE: PRT
<213> ORGANISM: Nicotiana tabacum

<400> SEQUENCE: 46

Ala Val Glu Leu Ile Asn Gly Arg Phe Asp Thr Glu Ala Ser Gly Asn
1 5 10 15

-continued

```
Val Thr Leu Glu Thr Val His Lys Ile Gly Gln Thr Gly Val Thr Tyr
            20                  25                  30

Ile Ser Ser Gly Ala Leu Thr His Ser Val Lys Ala Leu Asp
        35                  40                  45


<210> SEQ ID NO 47
<211> LENGTH: 20
<212> TYPE: PRT
<213> ORGANISM: Rhodospirillum rubrum

<400> SEQUENCE: 47

Asp Met Val Ala Leu Val Gly Ser Asp Ile Ala Ala Leu Ala Glu Ser
 1               5                  10                  15

Asp Val Thr Thr
            20


<210> SEQ ID NO 48
<211> LENGTH: 29
<212> TYPE: PRT
<213> ORGANISM: Mycobacterium lepre

<400> SEQUENCE: 48

Arg Arg Asp Ile Arg Ala Pro Thr Val Leu Leu Ser Gly Leu Ser Asn
 1               5                  10                  15

Ala Ala Ile Tyr Ala Gly Asp Tyr Leu Ala Val Arg Ile
            20                  25


<210> SEQ ID NO 49
<211> LENGTH: 21
<212> TYPE: PRT
<213> ORGANISM: Salmonella typhimurium

<400> SEQUENCE: 49

Lys Arg Val Gln Ala Arg Leu Val Ala Glu Leu Arg Glu Phe Ala Glu
 1               5                  10                  15

Asp Phe Val Gly Arg
            20


<210> SEQ ID NO 50
<211> LENGTH: 20
<212> TYPE: PRT
<213> ORGANISM: Escherichia coli

<400> SEQUENCE: 50

Lys Arg Thr Lys Ala Leu Leu Val Asp Lys Leu Arg Glu Phe Ala Glu
 1               5                  10                  15

Asp Phe Val Gln
            20


<210> SEQ ID NO 51
<211> LENGTH: 33
<212> TYPE: PRT
<213> ORGANISM: Homo sapiens

<400> SEQUENCE: 51

Leu Lys Ala Gln Phe Pro Ser Val Ala Val Glu Ala Gly Ile Thr Asp
 1               5                  10                  15

Asn Leu Pro Gln Phe Cys Gly Pro His Ile Asp Val Met Met Gln Ala
            20                  25                  30

Pro
```

-continued

<210> SEQ ID NO 52
<211> LENGTH: 44
<212> TYPE: PRT
<213> ORGANISM: Saccharomyces cerevisiae

<400> SEQUENCE: 52

Ser Leu Lys Asn Lys Trp Asn Gly Lys Lys His Phe Leu Leu Glu Cys
 1               5                  10                  15

Gly Leu Asn Asp Asn Leu Glu Glu Tyr Leu Cys Asp Asp Ile Asp Ile
            20                  25                  30

Tyr Thr Ser Ser Ile His Gln Gly Thr Pro Val Ile
        35                  40

<210> SEQ ID NO 53
<211> LENGTH: 20
<212> TYPE: PRT
<213> ORGANISM: Nicotiana tabacum

<400> SEQUENCE: 53

Ile Ser Lys Leu Ile Asp Thr Glu Leu Ala Leu Glu Val Gly Arg Arg
 1               5                  10                  15

Thr Lys Arg Ala
            20

<210> SEQ ID NO 54
<211> LENGTH: 12
<212> TYPE: PRT
<213> ORGANISM: Rhodospirillum rubrum

<400> SEQUENCE: 54

Gly Asp Val Val Ala Pro Pro Lys Ala Glu Arg Ala
 1               5                  10

<210> SEQ ID NO 55
<211> LENGTH: 6
<212> TYPE: PRT
<213> ORGANISM: Salmonella typhimurium

<400> SEQUENCE: 55

Leu Ser Met Arg Phe Cys
 1               5

<210> SEQ ID NO 56
<211> LENGTH: 6
<212> TYPE: PRT
<213> ORGANISM: Escherichia coli

<400> SEQUENCE: 56

Leu Ser Met Arg Phe Arg
 1               5

<210> SEQ ID NO 57
<211> LENGTH: 11
<212> TYPE: PRT
<213> ORGANISM: Homo sapiens

<400> SEQUENCE: 57

Phe Leu Phe Lys Val Ala Pro Val Pro Ile His
 1               5                  10

<210> SEQ ID NO 58
<211> LENGTH: 4
<212> TYPE: PRT

-continued

```
<213> ORGANISM: Saccharomyces cerevisiae

<400> SEQUENCE: 58

Phe Leu Ala His
 1
```

MODIFYING NICOTINE AND NITROSAMINE LEVELS IN TOBACCO

CROSS-REFERENCE TO RELATED APPLICATIONS

This application is a continuation of international application number PCT/US02/18040, and claims the benefit of priority of international application number PCT/US02/18040 having international filing date of Jun. 6, 2002, designating the United States of America and published in English, which claims the benefit of priority of U.S. provisional patent application No. 60/297,154, filed Jun. 8, 2001; both of which are hereby expressly incorporated by reference in their entireties.

FIELD OF THE INVENTION

The present invention generally relates to tobacco and tobacco products having a reduced amount of nicotine and/or tobacco specific nitrosamines (TSNA). More specifically, several ways to make tobacco plants that have reduced nicotine and TSNA levels have been discovered. Embodiments include tobacco harvested from said tobacco plants, cured tobacco from said tobacco plants, tobacco products made with said cured tobacco and methods of making these compositions.

BACKGROUND OF THE INVENTION

The health consequences of tobacco consumption are known but many people continue to use tobacco products. The addictive properties of tobacco products are largely attributable to the presence of nicotine. In addition to being one of the most addictive substances known, nicotine is also a precursor for a large number of carcinogenic compounds present in tobacco and the body.

There is currently great interest in methods for production of tobacco with decreased levels of noxious, carcinogenic, or addictive substances including tar, nitrosamines, and nicotine. Although researchers have developed several approaches to reduce the nicotine content or the nicotine delivery of tobacco products, many techniques result in a product that has poor taste, fragrance, or smoking properties. Some processes, for example, reduce the nicotine content of tobacco after it has been harvested through microbial enzymatic degradation, chemical treatment, or high pressure extraction. (See U.S. Pat. Nos. 4,557,280; 4,561,452; 4,848,373; 4,183,364; and 4,215,706, all of which are hereby expressly incorporated by reference in their entireties). In view of the foregoing, and notwithstanding the various efforts exemplified in the prior art, there remains a need for tobacco having reduced nicotine and TSNAs and methods of producing such tobacco.

SUMMARY OF THE INVENTION

Embodiments of the invention concern the production of tobacco and tobacco products having a reduced amount of nicotine and/or tobacco specific nitrosamines (TSNAs). In addition to having a reduced level of nicotine, some tobacco and tobacco products of the invention have reduced amounts of N'-nitrosonornicotine (NNN), N'-nitrosoanatabine (NAT), N'-nitrosoanabasine (NAB), 4-(N-nitrosomethylamino)-1-(3-pyridyl)-1-butanone (NNK), 4-(N-nitrosomethylamino)-4-(3-pyridyl)-1-butanal (NNA)-4-N-nitrosomethylamino)-1-(3-pyridyl)-1-butanol (NNAL), 4-N-nitrosomethylamino)-4-(3-pyridyl)-1-butanol (iso-NNAL) and/or 4-(N-nitrosomethylamino)-4-(3-pyridyl)-butanoic acid (iso-NNAC). Some embodiments, for example, are substantially free of at least one TSNA selected from the group consisting of N'-nitrosonornicotine, 4-(N-nitrosomethylamino)-1-(3-pyridyl)-1-butanone, N'-nitrosoanatabine, and N'-nitrosoanabasine. The term "tobacco products" include, but are not limited to, smoking materials (e.g., cigarettes, cigars, pipe tobacco), snuff, chewing tobacco, gum, and lozenges. One embodiment, for example, includes a genetically modified cured tobacco comprising a reduced amount of nicotine and a collective content of NNN, NAT, NAB, and NNK of less than about 0.5 $\mu$g/g, 0.4 $\mu$g/g or 0.2 $\mu$g/g. That is, said cured tobacco is made from a genetically modified tobacco plant.

Another aspect of the invention concerns methods to substantially eliminate or reduce the amount of nicotine and/or TSNAs in tobacco. By one approach, tobacco plants are made substantially free of nicotine by interrupting the ability of the plant to synthesize nicotine using genetic engineering. Some embodiments comprise cured tobacco and tobacco products wherein the amount of nicotine is less than about 2 mg/g, 1 mg/g, 0.75 mg/g, 0.5 mg/g or desirably less than about 0.1 mg/g. By virtue of the elimination of nicotine in these genetically modified plants, tobacco and tobacco products made from these plants also have a reduced amount of TSNAs. In a preferred method, transgenic tobacco is created to have one or more TSNAs reduced including, but not limited to, N'-nitrosonornicotine (NNN), 4-(N-nitrosomethylamino)-1-(3-pyridyl)-1-butanone (NNK), N'-nitrosoanatabine (NAT), and/or N'-nitrosoanabasine (NAB). Tobacco products including, but not limited to, smoking materials (e.g., cigarettes, cigars, pipe tobacco), snuff, chewing tobacco, gum and lozenges are then prepared from said transgenic tobacco plants using conventional techniques. Preferably these tobacco products are manufactured from harvested tobacco leaves and stems that have been cut, dried, cured, and/or fermented according to conventional techniques in tobacco preparation. However, modified techniques in curing and tobacco processing can also be implemented to further lower the levels of TSNAs.

In some embodiments of the invention, the tobacco that is substantially free of nicotine and TSNAs is made by exposing at least one tobacco cell of a selected variety to an exogenous DNA construct having, in the 5' to 3' direction, a promoter operable in a plant cell and DNA containing a portion of a DNA sequence that encodes an enzyme in the nicotine synthesis pathway. The DNA is operably associated with said promoter, the tobacco cell is transformed with the DNA construct, the transformed cells are selected and at least one transgenic tobacco plant is regenerated from the transformed cells. The transgenic tobacco plants contain a reduced amount of nicotine and/or TSNAs as compared to a control tobacco plant of the same variety. In preferred embodiments, DNA constructs having a portion of a DNA sequence that encodes an enzyme in the nicotine synthesis pathway may have the entire coding sequence of the enzyme, or any portion thereof.

In some embodiments, the enzyme involved in the nicotine synthesis pathway is putrescine N-methyltransferase, N-methylputrescine oxidase, ornithine decarboxylase, S-adenosylmethionine synthetase, NADH dehydrogenase, phosphoribosylanthranilate isomerase or quinolate phosphoribosyl transferase (QPTase). In a preferred embodiment, the enzyme is QPTase. The segment of DNA sequence encoding an enzyme in the nicotine synthesis pathway may be in the antisense or the sense orientation. In some embodiments, the tobacco that is made substantially free of nicotine and/or TSNAs is prepared from a variety of Burley tobacco (e.g., Burley 21), Oriental tobacco, or Flue-cured tobacco. It should be understood, however, that most tobacco varieties can be made to be nicotine and/or TSNA free using the embodiments described herein. For example, plant cells of the variety Burley 21 are used as the host for the genetic engineering that results in the reduction of nicotine and/or TSNAs so that the resultant transgenic plants are a Burley 21 variety that has a reduced amount of nicotine and/or TSNAs.

An aspect of the invention also includes an isolated DNA molecule comprising SEQ ID NO: 1, DNA sequences which encode an enzyme having SEQ ID NO: 2, DNA sequences that hybridize to such DNA and encode a quinolate phosphoribosyl transferase enzyme or a portion of such an enzyme and DNA sequences which differ from the above DNA due to the degeneracy of the genetic code. A peptide encoded by such DNA is a further aspect of the invention.

A further aspect of the present invention concerns a DNA construct comprising a promoter operable in a plant cell and a DNA segment encoding a quinolate phosphoribosyl transferase enzyme positioned downstream from the promoter and operatively associated therewith. The DNA encoding the enzyme may be in the antisense or sense direction.

A further aspect of the present invention involves a method of making a transgenic plant cell having reduced quinolate phosphoribosyl transferase (QPTase) expression, by providing a plant cell of a type known to express quinolate phosphoribosyl transferase; transforming the plant cell with an exogenous DNA construct comprising a promoter and DNA comprising a portion of a sequence encoding quinolate phosphoribosyl transferase mRNA. In preferred embodiments, DNA constructs having a portion of a DNA sequence encoding quinolate phosphoribosyl transferase may have the entire coding sequence of the enzyme, or any portion thereof. More preferred are tobaccos containing genetic modification comprising a sequence corresponding to the quinolate phosphoribosyl transferase (QPTase) gene or a fragment thereof at least 13 nucleotides in length.

A further aspect of the present invention concerns a transgenic plant of the species *Nicotiana* having reduced quinolate phosphoribosyl transferase (QPTase) expression relative to a non-transformed control plant. The cells of such plants comprise a DNA construct that includes a DNA sequence that encodes a plant quinolate phosphoribosyl transferase mRNA or some portion thereof.

A further aspect of the present invention involves a method for reducing expression of a quinolate phosphoribosyl transferase gene in a plant cell by growing a plant cell transformed to contain exogenous DNA, where a transcribed strand of the exogenous DNA is complementary to quinolate phosphoribosyl transferase mRNA endogenous to the cell. Transcription of the complementary strand reduces expression of the endogenous quinolate phosphoribosyl gene.

A further aspect of the present invention includes a method of producing a tobacco plant having decreased levels of nicotine in leaves of the tobacco plant by regenerating a tobacco plant from cells that comprise an exogenous DNA sequence that encodes an RNA that is complementary to a region of endogenous quinolate phosphoribosyl transferase messenger RNA in the cells.

A further aspect of the invention concerns a method of producing a tobacco plant having reduced nicotine and/or TSNAs, which involves regenerating a tobacco plant from cells that comprise an exogenous DNA sequence, where a transcribed strand of the exogenous DNA sequence is complementary to a region of endogenous quinolate phosphoribosyl transferase messenger RNA in the cells. Related embodiments include methods of producing tobacco products from said tobacco plant that have a reduced amount of nicotine and/or TSNAs, said tobacco products including, but are not limited to, cigarettes, cigars, pipe tobacco, chewing tobacco, and may be in the form of leaf tobacco, shredded tobacco, or cut tobacco.

A further aspect of the invention concerns the manufacture, isolation, and/or characterization of tobacco mutants that exhibit a mutation in a gene involved in nicotine biosynthesis that results in a tobacco plant that has a reduced amount of nicotine and/or TSNAs. Some embodiments, for example, have a mutation in at least one gene involved in nicotine biosynthesis including, but not limited to, putrescine N-methyltransferase, N-methylputrescine oxidase, ornithine decarboxylase, S-adenosylmethionine synthetase, NADH dehydrogenase, phosphoribosylanthranilate isomerase, or quinolate phosphoribosyl transferase (QPTase). Natural mutants in the above genes can be selected for reduced levels of nicotine and/or TSNAs using techniques common to plant breeding. In some embodiments, the tobacco mutants above are prepared from a variety of Burley tobacco (e.g., Burley 21), Oriental tobacco, or Flue-cured tobacco. It should be understood, however, that mutants of genes in nicotine biosynthesis can be selected from most tobacco varieties. These tobacco plants can also be used to prepare tobacco products that have reduced levels of nicotine and/or TSNAs.

Additional embodiments include tobacco products that have been carefully blended so that desired levels of nicotine and/or TSNAs are obtained. For example, tobacco having a reduced level of nicotine and/or TSNAs, prepared as described above, can be blended with conventional tobacco so as to obtain virtually any amount of nicotine and/or TSNAs. Further, two or more varieties of tobacco having a reduced level of nicotine and/or TSNAs can be blended so as to achieve a desired amount of nicotine and/or TSNAs. In this manner, differences in variety, flavor, as well as amounts of nicotine and/or TSNAs can be incrementally adjusted. These blended tobacco products can be incorporated into tobacco use cessation kits and programs designed to reduce or eliminate nicotine dependence and carcinogenic potential. Such kits and programs are also embodiments of the invention.

More embodiments of the invention concern methods to reduce the carcinogenic potential of tobacco products, including cigarettes, cigars, chewing tobacco, snuff and tobacco-containing gum and lozenges. Some methods, for example involve the preparation of tobacco having a reduced amount of nicotine and/or TSNAs and the manufacture of tobacco products containing said tobacco. Accordingly, the transgenic tobacco plants, described above, are harvested, cured, and processed into tobacco products. These tobacco products have a reduced carcinogenic potential because they are prepared from tobacco that has a reduced amount of nicotine and/or TSNAs.

Yet another aspect of the invention concerns the reduction of the amount of TSNAs, preferably NNN and NNK, and metabolites thereof in humans who smoke, consume or otherwise ingest tobacco. This method is practiced by providing a tobacco product having a reduced amount of TSNAs to said humans, thereby lowering the carcinogenic potential of such product in said humans. By one approach, for example, the carcinogenic potential of side stream or main stream tobacco smoke in a human exposed to said side stream or main stream tobacco smoke is reduced by providing the cured tobacco as described above in a product that undergoes pyrolysis, wherein pyrolysis of said product results in side stream or main stream smoke comprising a reduced amount of TSNAs. Thus, the cured tobacco described above can be used to prepare a tobacco smoking product that produces a reduced amount of TSNAs in the side stream and/or mainstream smoke and thereby reduce the amount of carcinogen in humans who come in contact with tobacco smoke.

BRIEF DESCRIPTION OF THE DRAWINGS

FIG. 2A provides the nucleic acid sequence of NtQPT1 cDNA (SEQ ID NO: 1), with the coding sequence (SEQ ID NO: 3) shown in capital letters.

FIG. 2B provides the deduced amino acid sequence (SEQ ID NO: 2) of the tobacco QPTase encoded by NtQPT1 cDNA.

FIG. 3 aligns the deduced NtQPT1 amino acid sequence and related sequences of *Rhodospirillum rubrum, Mycobacterium lepre, Salmonella typhimurium, Escherichia coli*, human, and *Saccharomyces cerevisiae.*

DETAILED DESCRIPTION OF THE INVENTION

Figure 1:
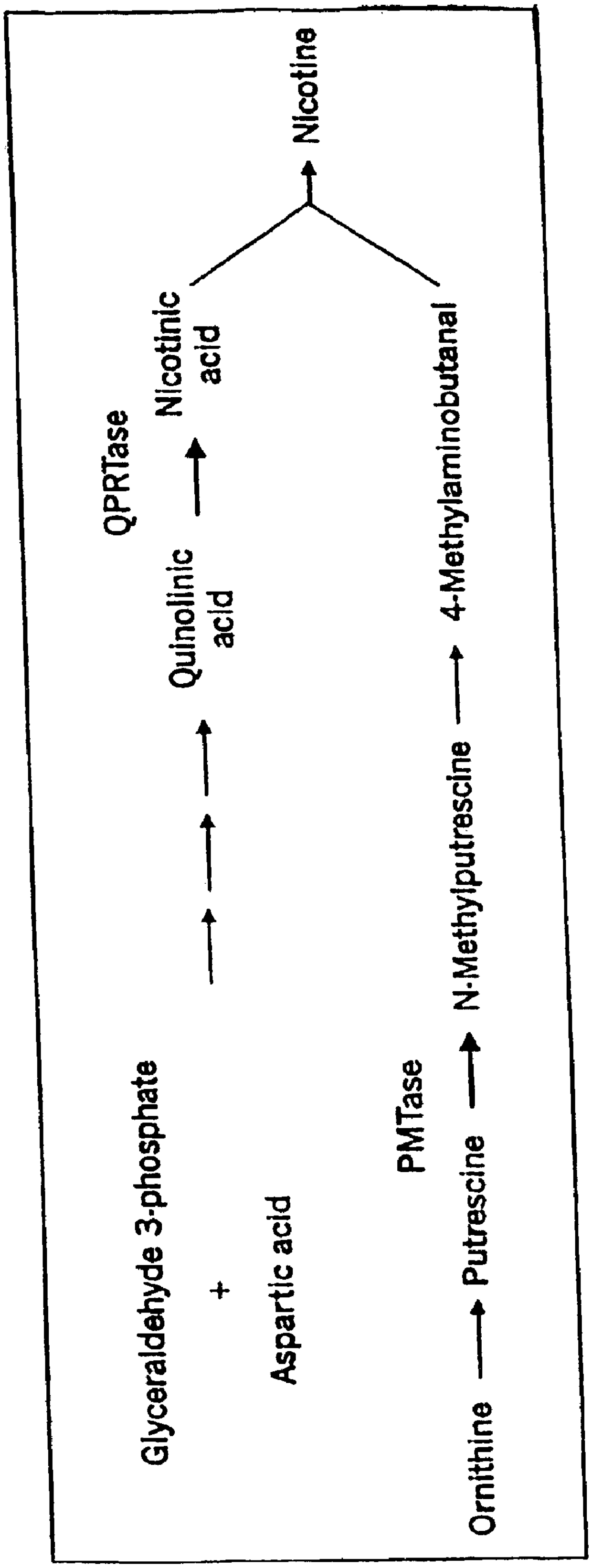
FIG. 1 shows the biosynthetic pathway leading to nicotine. Enzyme activities known to be regulated by Nic1 and Nic2 are QPTase (quinolate phosphoribosyl transferase) and PMTase (putrescence methyl-transferase).

Several approaches to create tobacco and tobacco products that have a reduced amount of nicotine and/or TSNAs have been discovered. Aspects of the technology described herein are also described in PCT/US98/11893, which is hereby expressly incorporated by reference in its entirety. By one approach, transgenic tobacco plants that have reduced nicotine and TSNA levels are created and tobacco harvested from said transgenic tobacco plants is used to prepare a variety of tobacco products. One such transgenic tobacco plant comprises a DNA construct that encodes an antisense RNA that complements at least a portion of the quinolate phosphoribosyl transferase (QPTase) gene. Transcription of the complementary strand of RNA reduces expression of the endogenous quinolate phosphoribosyl gene, which, in turn, reduces the amount of nicotine and, concomitantly, the amount of TSNA in the tobacco plant. Thus, one inventive concept is that reducing the nicotine content in a tobacco plant using genetic engineering can reduce TSNA content in said plant. The section below provides more description on nitrosamines and tobacco-specific nitrosamines.

Nitrosamines and Tobacco-specific Nitrosamines

The term nitrosamine generally refers to any of a class of organic compounds with the general formula $R_2NNO$ or RNHNO (where R denotes an amine-containing group). Nitrosamines are present in numerous foods and have been found to be carcinogenic in laboratory animals. These compounds are formed by nitrosation reactions of amines such as amino acids and alkaloids with nitrites and/or nitrous oxides. By themselves, nitrosamines are not carcinogenic substances, but in mammals nitrosamines undergo decomposition by enzymatic activation to form alkylating metabolites which appear to react with biopolymers to initiate their tumorogenic effect. Thus, by reducing the amount of nitrosamine intake, one has effectively reduced the carcinogenic potential in humans.

Nitrosamines have been identified in tobacco, tobacco products, and tobacco smoke by the use of techniques such as gas chromatography-thermal exchange analysis (GC-TEA). Some of these nitrosamines have been identified as tobacco-specific nitrosamines (TSNAs). TSNAs are primarily formed by reactions between the two most abundant alkaloids, nicotine and nornicotine, with nitrous oxides (NOx), and they account proportionately for the highest concentration of nitrosamines in both tobacco products and in mainstream smoke. Of the TSNAs identified, and the subset that have been found to be present in cigarette smoke, the most characterized is N-nitrosamine, 4-(methylnitrosamino)-1-(3-pyridyl)-1-butanone (N-nitrosamine-ketone), or NNK. When injected at relatively high doses, NNK is carcinogenic in rodents. Minimal amounts of TSNAs are found in green tobacco, indicating that TSNA formation may occur during processing steps such as curing, drying, fermentation, burning or storage of tobacco.

TSNA formation is attributed to chemical, enzymatic and bacterial influences during tobacco processing, particularly during curing, fermentation and aging. Nitrosation of nornicotine, anatabine, and anabasine gives the corresponding nitrosamines: N'-nitrosonornicotine (NNN), N'-nitrosoanatabine (NAT) and N'-nitrosoanabasine (NAB). Nitrosation of nicotine in aqueous solution affords a mixture of 4-(N-nitrosomethylamino)-1-(3-pyridyl)-1-butanone (NNK), NNN, and 4-(N-nitrosomethylamino)-4-(3-pyridyl)-1-butanal (NNA). Less commonly encountered TSNAs include NNAL (4-N-nitrosomethylamino)-1-(3-pyridyl)-1-butanol), iso-NNAL (4-N-nitrosomethylamino)-4-(3-pyridyl)-1-butanol, 11) and iso-NNAC (4-(N-nitrosomethylamino)-4-(3-pyridyl)-butanoic acid, 12). See, U.S. Pat. No. 6,135,121, the entire disclosure of which is hereby expressly incorporated by reference in its entirety.

TSNA levels are particularly high in chewing tobaccos and snuff. The partially anaerobic processes that occur during fermentation promote the formation of TSNAs from tobacco alkaloids by promoting increased nitrite levels; in particular, over-fermentation can increase TSNA levels in snuff by its effects on nitrate levels and microbial enzymatic activity. The reduction of the nitrosamine level in snuff in recent years has been achieved by maintaining a better control over the bacterial content in these products.

Since the nitrate level of tobacco is important for nitrosamine formation in cigarette smoke, a significant reduction of nitrosamines in smoke can be achieved by low-nitrate leaf and stem blends. However, these methods may negatively impact the smokability or the taste of the tobacco. The nitrosamine content of mainstream smoke can be reduced by as much as 80% by cellulose acetate filters, and it can be reduced still further by filter ventilation.

Air-cured tobaccos such as burley and dark-fired may have higher levels of TSNAs than certain types of flue-cured bright, burley, or dark tobaccos apparently because the high temperatures associated with flue-curing can kill the microorganisms that transform the alkaloids into TSNAs. In air-cured types, nitrate ($N—NO_3$) is more abundant in the leaf (particularly in the leaf and stems) than in flue-cured tobacco and the alkaloid content is also much higher. This $N—NO_3$ is reduced to nitrite ($NO_2^-$) by microbes during curing and the $NO_2^-$ can be further reduced to NOx or react directly with alkaloids to form TSNAs.

It is contemplated that, in addition to the techniques described above, nitrate levels in tobacco (especially in the leaf) can be reduced by limiting exposure to nitrosating agents or conditions. Air-curing experiments at a higher temperature have shown that considerably higher levels of N-nitrosamines are formed at a curing temperature of 32° C. than at 16° C., which is associated with a rise of the nitrite level in the tobacco, and may also be associated with a rise in microbial enzymatic activity. Modified curing that involves faster drying from wider spacing or from more open curing structures has been shown to reduce TSNA levels in burley tobacco. The climatic conditions prevailing during curing exert a major influence on N-nitrosamine formation, and the relative humidity during air-curing can be of importance. Stalk curing results in higher TSNA levels in the smoke than primed-leaf curing. Sun-cured Oriental tobaccos have lower TSNA levels than Flue and air-cured dark tobaccos. Accelerated curing of crude tobaccos such as homogenized leaf curing limits the ability of bacteria to carry out the nitrosation reactions. However, many of the methods described above for reducing TSNAs in Burley tobacco can have undesirable effects on tobacco taste.

TSNA formation in flue-cured tobacco also results from exposure of the tobacco to combustion gases during curing, where nearly all of the TSNAs in flue-cured tobacco (e.g., Virginia Flue) result from a reaction involving NOx and nicotine. The predominant source of NOx is the mixture of combustion gases in direct-fired barns. At present, flue-cured tobacco is predominantly cured in commercial bulk barns. As a result of energy pressures in the U.S. during the 1960's, farmer-built "stick barns" with heat-exchanged flue systems were gradually replaced with more energy efficient bulk barns using direct-fired liquid propane gas (LPG) burners. These LPG direct-fired burner systems exhaust combustion gases and combustion by-products directly into the barn where contact is made with the curing tobacco. Studies indicate that LPG combustion by-products react with naturally occurring tobacco alkaloids to form TSNA.

In contrast to direct-fired curing, heat-exchange burner configurations completely vent combustion gases and combustion by-products to the external atmosphere rather than into the barn. The heat-exchange process precludes exposure of the tobacco to LPG combustion by-products, thereby eliminating an important source of nitrosating agent for TSNA formation, without degrading leaf quality or smoking quality. The use of heat exchangers reduces TSNA levels by about 90%. Steps are being taken to reduce TSNA levels in US tobacco by converting barns to indirect heat through the use of a heat exchanger, but these methods are very expensive. Although many of the approaches described in this section have significant drawbacks, it should be understood that any or all of these techniques can be used with other techniques, as described herein, to make tobacco and tobacco products having reduced nitrosamines. The section below provides more detail on nicotine and approaches to reduce nicotine in tobacco.

Nicotine

Nicotine is formed primarily in the roots of the tobacco plant and is subsequently transported to the leaves, where it is stored (Tso, Physiology and Biochemistry of Tobacco Plants, pp. 233–34, Dowden, Hutchinson & Ross, Stroudsburg, Pa. (1972)). Classical crop breeding techniques have produced tobacco with lower levels of nicotine, including varieties with as low as 8% of the amount of nicotine found in wild-type tobacco. The many methods described herein can be used with virtually any tobacco variety but are preferably used with burley, oriental or Flue (e.g., Virginia Flue) varieties.

Nicotine is produced in tobacco plants by the condensation of nicotinic acid and 4-methylaminobutanal. The biosynthetic pathway resulting in nicotine production is illustrated in FIG. 1. Two regulatory loci (Nic1 and Nic2) act as co-dominant regulators of nicotine production. Enzyme analyses of root tissue from single and double Nic mutants show that the activities of two enzymes, quinolate phosphoribosyl transferase ("QPTase") and putrescence methyl transferase (PMTase), are directly proportional to levels of nicotine biosynthesis. An obligatory step in nicotine biosynthesis is the formation of nicotinic acid from quinolinic acid, a step that is catalyzed by QPTase. QPTase appears to be a rate-limiting enzyme in the pathway supplying nicotinic acid for nicotine synthesis in tobacco. (See, eg., Feth et al., *Planta,* 168, pp. 402–07 (1986) and Wagner et al., *Physiol. Plant.,* 68, pp. 667–72 (1986), herein expressly incorporated by reference in its entirety). A comparison of enzyme activity in tobacco tissues (root and callus) with different capacities for nicotine synthesis shows that QPTase activity is strictly correlated with nicotine content (Wagner and Wagner, Planta 165:532 (1985), herein expressly incorporated by reference in its entirety). In fact, Saunders and Bush (Plant Physiol 64:236 (1979), herein expressly incorporated by reference in its entirety), showed that the level of QPTase in the roots of low nicotine mutants is proportional to the level of nicotine in the leaves.

The modification of nicotine levels in tobacco plants by antisense regulation of putrescence methyl transferase (PMTase) expression has been proposed in U.S. Pat. Nos. 5,369,023 and 5,260,205, to Nakatani and Malik, and in PCT application WO 94/28142 to Wahad and Malik, which describe DNA encoding PMT and the use of sense and antisense PMT constructs, the entire disclosures of each of which are hereby expressly incorporated by reference in their entireties. Other genetic modifications proposed to reduce nicotine levels are described in PCT application WO 00/67558, to Timko, and WO 93/05646, to Davis and Marcum; the entire contents of each are hereby expressly incorporated by reference in their entireties. Although many of the approaches described in this section have significant drawbacks, it should be understood that any or all of these techniques can be used with other techniques, as described herein, to make tobacco and tobacco products having reduced nicotine. The section below explains novel approaches to reduce the amount of nicotine and TSNAs in tobacco and tobacco products.

Reducing the Amount of Nicotine and Tobacco Specific Nitrosamines (TSNAs)

As discussed above, TSNAs and nicotine contribute significantly to the carcinogenic potential and addictive properties of tobacco and tobacco products. Thus, tobacco and tobacco products that have reduced amounts of TSNAs and nicotine have tremendous utility. Without wishing to be bound by any particular theory, it is contemplated that the creation of tobacco plants, tobacco and tobacco products that have a reduced amount of nicotine will also have reduced amounts of TSNAs. That is, by removing nicotine from tobacco plants, tobacco and tobacco products, one effectively removes the alkaloid substrate for TSNA formation. It was found that the reduction of nicotine in tobacco was directly related to the reduction of TSNAs. Unexpectedly, the methods described herein not only produce tobacco with a reduced addictive potential but, concomitantly, produce a tobacco that has a lower carcinogenic potential.

It should be emphasized that the phrase "a reduced amount" is intended to refer to an amount of nicotine and/or TSNAs in a treated or transgenic tobacco plant, tobacco or a tobacco product that is less than what would be found in a tobacco plant, tobacco or a tobacco product from the same variety of tobacco, processed in the same manner, which has not been treated or was not made transgenic for reduced nicotine and/or TSNAs. Thus, in some contexts, wild-type tobacco of the same variety that has been processed in the same manner is used as a control by which to measure whether a reduction in nicotine and/or TSNAs has been obtained by the inventive methods described herein.

The amount of TSNAs (e.g., collective content of NNN, NAT, NAB, and NNK) and nicotine in wild-type tobacco varies significantly depending on the variety and the manner it is grown, harvested and cured. For example, a cured Burley tobacco leaf can have approximately 30,000 parts per million (ppm) nicotine and 8,000 parts per billion (ppb) TSNA (e.g., collective content of NNN, NAT, NAB, and NNK); a Flue-Cured leaf can have approximately 20,000 ppm nicotine and 300 ppb TSNA (e.g., collective content of NNN, NAT, NAB, and NNK); and an Oriental cured leaf can have approximately 10,000 ppm nicotine and 100 ppb TSNA (e.g., collective content of NNN, NAT, NAB, and NNK). Tobacco having a reduced amount of nicotine and/or TSNA, can have no detectable nicotine and/or TSNA (e.g., collective content of NNN, NAT, NAB, and NNK), or may contain some detectable amounts of one or more of the TSNAs and/or nicotine, so long as the amount of nicotine and/or TSNA is less than that found in tobacco of the same variety, grown under similar conditions, and cured and/or processed in the same manner. That is, cured Burley tobacco, as described herein, having a reduced amount of nicotine can have between 0 and 30,000 ppm nicotine and 0 and 8,000 ppb TSNA, desirably between 0 and 20,000 ppm nicotine and 0 and 6,000 ppb TSNA, more desirably between 0 and 10,000 ppm nicotine and 0 and 5,000 ppb TSNA, preferably between 0 and 5,000 ppm nicotine and 0 and 4,000 ppb TSNA, more preferably between 0 and 2,500 ppm nicotine and 0 and 2,000 ppb TSNA and most preferably between 0 and 1,000 ppm nicotine and 0 and 1,000 ppb TSNA. Embodiments of cured Burley leaf prepared by the methods described herein can also have between 0 and 1000 ppm nicotine and 0 and 500 ppb TSNA, 0 and 500 ppm nicotine and 0 and 250 ppb TSNA, 0 and 250 ppm nicotine and 0 and 100 ppb TSNA, 0 and 100 ppm nicotine and 0 and 50 ppb TSNA, 0 and 50 ppm nicotine and 0 and 5 ppb TSNA and some embodiments of cured Burley leaf described herein have virtually no detectable amount of nicotine or TSNA. In some embodiments above, the amount of TSNA refers to the collective content of NNN, NAT, NAB, and NNK.

Similarly, a cured Flue tobacco embodiment of the invention having a reduced amount of nicotine can have between 0 and 20,000 ppm nicotine and 0 and 300 ppb TSNA, desirably between 0 and 15,000 ppm nicotine and 0 and 250 ppb TSNA, more desirably between 0 and 10,000 ppm nicotine and 0 and 200 ppb TSNA, preferably between 0 and 5,000 ppm nicotine and 0 and 150 ppb TSNA, more preferably between 0 and 2,500 ppm nicotine and 0 and 100 ppb TSNA and most preferably between 0 and 1,000 ppm nicotine and 0 and 50 ppb TSNA. Embodiments of cured Flue tobacco, as described herein, can also have between 0 and 500 ppm nicotine and 0 and 25 ppb TSNA, 0 and 200 ppm nicotine and 0 and 10 ppb TSNA, 0 and 100 ppm nicotine and 0 and 5 ppb TSNA and some embodiments of cure Flue tobacco have virtually no detectable amount of nicotine or TSNA. In some embodiments above, the amount of TSNA refers to the collective content of NNN, NAT, NAB, and NNK.

Further, a cured Oriental tobacco embodiment having a reduced amount of nicotine can have between 0 and 10,000 ppm nicotine and 0 and 100 ppb TSNA, desirably between 0 and 7,000 ppm nicotine and 0 and 75 ppb TSNA, more desirably between 0 and 5,000 ppm nicotine and 0 and 50 ppb TSNA, preferably between 0 and 3,000 ppm nicotine and 0 and 25 ppb TSNA, more preferably between 0 and 1,500 ppm nicotine and 0 and 10 ppb TSNA and most preferably between 0 and 500 ppm nicotine and no detectable TSNA. Embodiments of cured Oriental tobacco can also have between 0 and 250 ppm nicotine and no detectable TSNA and some embodiments of cured Oriental tobacco have virtually no detectable amount of nicotine or TSNA. In some embodiments above, the amount of TSNA refers to the collective content of NNN, NAT, NAB, and NNK.

Some embodiments comprise cured tobaccos (e.g., Burley, Flue, or Oriental) with reduced amounts of nicotine as compared to control varieties, wherein the amount of nicotine is less than about 2 mg/g, 1 mg/g, 0.75 mg/g, 0.5 mg/g or desirably less than about 0.1 mg/g, and preferably less than 0.08 mg/g, 0.07 mg/g, 0.06 mg/g, 0.05 mg/g, 0.04 mg/g, 0.03 mg/g, 0.02 mg/g, 0.01 mg/g. Tobacco products made from these reduced nicotine and TSNA tobaccos are also embodiments. The term "tobacco products" include, but are not limited to, smoking materials (e.g., cigarettes, cigars, pipe tobacco), snuff, chewing tobacco, gum, and lozenges.

In some contexts, the phrase "reduced amount of nicotine and/or TSNAs" refers to the tobacco plants, cured tobacco, and tobacco products, as described herein, which have less nicotine and/or TSNAs (e.g., the collective content of NNN, NAT, NAB, and NNK) by weight than the same variety of tobacco grown, processed, and cured in the same way. For example, wild type cured tobacco can have has approximately 1–4% dry weight nicotine and approximately 0.2%–0.8% dry weight TSNA depending on the manner it was grown, harvested and cured. A typical cigarette has between 2–11 mg of nicotine and approximately 5.0 $\mu$g of TSNAs. Thus, the tobacco plants, tobacco and tobacco products of the invention can have, in dry weight for example, less than 0.01%, 0.015%, 0.02%, 0.025%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.55%, 0.6%, 0.65%, 0.7%, 0.75%, 0.8%, 0.85%, 0.9%, 0.95%, and 1.0% nicotine and less than 0.01%, 0.015%, 0.02%, 0.025%, 0.03%, 0.035%, 0.04%, 0.045%, 0.05%, 0.055%, 0.06%, 0.065%, 0.07%, 0.075%, and 0.08% TSNA (e.g., collective content of NNN, NAT, NAB, and NNK).

Alternatively, a cigarette of the invention can have, for example, less than 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg, 1.0 mg, 1.1 mg, 1.15 mg, 1.2 mg, 1.25 mg, 1.3 mg, 1.35 mg, 1.4 mg, 1.45 mg, 1.5 mg, 1.55 mg, 1.6 mg, 1.65 mg, 1.7 mg, 1.75 mg, 1.8 mg, 1.85 mg, 1.9 mg, 1.95 mg, 2.0 mg, 2.1 mg, 2.15 mg, 2.2 mg, 2.25 mg, 2.3 mg, 2.35 mg, 2.4 mg, 2.45 mg, 2.5 mg, 2.55 mg, 2.6 mg, 2.65 mg, 2.7 mg, 2.75 mg, 2.8 mg, 2.85 mg, 2.9 mg, 2.95 mg, 3.0 mg, 3.1 mg, 3.15 mg, 3.2 mg, 3.25 mg, 3.3 mg, 3.35 mg, 3.4 mg, 3.45 mg, 3.5 mg, 3.55 mg, 3.6 mg, 3.65 mg, 3.7 mg, 3.75 mg, 3.8 mg, 3.85 mg, 3.9 mg, 3.95 mg, 4.0 mg,. 4.1 mg, 4.15 mg, 4.2 mg, 4.25 mg, 4.3 mg, 4.35 mg, 4.4 mg, 4.45 mg, 4.4 mg, 4.45 mg, 4.5 mg, 4.55 mg, 4.6 mg, 4.65 mg, 4.7 mg, 4.75 mg, 4.8 mg, 4.85 mg, 4.9 mg, 4.95 mg, 5.0 mg, 5.5 mg, 5.7 mg, 6.0 mg, 6.5 mgmg, 6.7 mg, 7.0 mg, 7.5 mg, 7.7 mg, 8.0 mg, 8.5 mg, 8.7 mg, 9.0 mg, 9.5 mg, 9.7 mg, 10.0 mg, 10.5 mg, 10.7 mg, and 11.0 mg nicotine and less than 0.001 ug, 0.002 ug, 0.003 ug, 0.004 ug, 0.005 ug, 0.006 ug, 0.007 ug, 0.008 ug, 0.009 ug, 0.01 ug, 0.02 ug, 0.03 ug, 0.04 ug, 0.05 ug, 0.06 ug, 0.07 ug, 0.08 ug, 0.09 ug, 0.1 ug, 0.15 ug, 0.2 ug, 0.25 ug, 0.3 ug, 0.336 ug, 0.339 ug, 0.345 ug, 0.35 ug, 0.375 ug, 0.4 ug, 0.414 ug, 0.45 ug, 0.5 ug, 0.515 ug, 0.55 ug, 0.555 ug, 0.56 ug, 0.578 ug, 0.58 ug, 0.6 ug, 0.61 lug, 0.624 ug, 0.65 ug, 0.7 ug, 0.75 ug, 0.8 ug, 0.85 ug, 0.9 ug, 0.95 ug, 1.0 ug, 1.1 ug, 1.114 ug, 1.15 ug, 1.2 ug, 1.25 ug, 1.3 ug, 1.35 ug, 1.4 ug, 1.45 ug, 1.5 ug, 1.55 ug, 1.6 ug, 1.65 ug, 1.7 ug, 1.75 ug, 1.8 ug, 1.85 ug, 1.9 ug, 1.95 ug, 2.0 ug, 2.1 ug, 2.15 ug, 2.2 ug TSNA (e.g., collective content of NNN, NAT, NAB, and NNK).

Unexpectedly, it was discovered that several methods for reducing endogenous levels of nicotine in a plant are suitable for producing tobacco that is substantially free of nitrosamines, especially TSNAs. Any method that reduces levels of other alkaloids, including norniticotine, will likewise be suitable for producing tobacco substantially free of nitrosamines, especially TSNAs. As described this invention comprises a method of reducing the carcinogenic potential of a tobacco product comprising providing a cured tobacco as described herein and preparing a tobacco product from said cured tobacco, whereby the carcinogenic potential of said tobacco product is thereby reduced. Other embodiments of the invention include the use of the cured tobacco described herein for the preparation of a tobacco product that contains reduced amounts of carcinogens as compared to control varieties and/or that reduces the amount of a TSNA or TSNA metabolite in a human that uses tobacco.

In some embodiments, for example, the tobacco smoking products described herein reduce the carcinogenic potential of side stream or main stream tobacco smoke in humans exposed to said side stream or main stream tobacco smoke. By providing the genetically modified cured tobacco described herein in a product that undergoes pyrolysis, for example, the side stream and/or main stream smoke produced by said product comprises a reduced amount of TSNAs and/or nicotine. Thus, the cured tobacco described herein can be used to prepare a tobacco smoking product that comprises a reduced amount of TSNAs in side stream and/or mainstream smoke.

In some embodiments, for example, the collective content of NNN, NAT, NAB, and NNK in the mainstream or side stream smoke from a tobacco product comprising the genetically modified tobacco described herein is between about 0–5.0 μg/g, 0–4.0 μg/g, 0–3.0 μg/g, 0–2.0 μg/g, 0–1.5 μg/g, 0–1.0 μg/g, 0–0.75 μg/g, 0–0.5 μg/g, 0–0.25 μg/g, 0–0.15 μg/g, 0–0.1 μg/g, 0–0.05 μg/g, 0–0.02 μg/g, 0–0.015 μg/g, 0–0.01 μg/g, 0–0.005 μg/g, 0–0.002 μg/g, or 0–0.001 μg/g. That is, some embodiments are genetically modified Burley tobacco, wherein the side stream or mainstream smoke produced from a tobacco product comprising said Burley tobacco has a collective content of NNN, NAT, NAB, and NNK in the mainstream or side stream smoke between about 0–5.0 μg/g, 0–4.0 μg/g, 0–3.0 μg/g, 0–2.0 μg/g, 0–1.5 μg/g, 0–1.0 μg/g, 0–0.75 μg/g, 0–0.5 μg/g, 0–0.25 μg/g, 0–0.15 μg/g, 0–0.1 μg/g, 0–0.05 μg/g, 0–0.02 μg/g, 0–0.015 μg/g, 0–0.01 μg/g, 0–0.002 μg/g, or 0–0.001 μg/g.

Other embodiments concern genetically modified Flue tobacco, wherein the sidestream or mainstream smoke produced from a tobacco product comprising said Flue tobacco has a collective content of NNN, NAT, NAB, and NNK in the mainstream or side stream smoke between about 0–5.0 μg/g, 0–4.0 μg/g, 0–3.0 μg/g, 0–2.0 μg/g, 0–1.5 μg/g, 0–1.0 μg/g, 0–0.75 μg/g, 0–0.5 μg/g, 0–0.25 μg/g, 0–0.15 μg/g, 0–0.1 μg/g, 0–0.05 μg/g, 0–0.02 μg/g, 0–0.015 μg/g, 0–0.01 μg/g, 0–0.002 μg/g, or 0–0.001 μg/g.

More embodiments concern genetically modified Oriental tobacco, wherein the sidestream or mainstream smoke produced from a tobacco product comprising said Oriental tobacco has a collective content of NNN, NAT, NAB, and NNK in the mainstream or side stream smoke between about 0–5.0 μg/g, 0–4.0 μg/g, 0–3.0 μg/g, 0–2.0 μg/g, 0–1.5 μg/g, 0–1.0 μg/g, 0–0.75 μg/g, 0–0.5 μg/g, 0–0.25 μg/g, 0–0.15 μg/g, 0–0.1 μg/g, 0–0.05 μg/g, 0–0.02 μg/g, 0–0.015 μg/g, 0–0.01 μg/g, 0–0.005 μg/g 0–0.002 μg/g, or 0–0.001 μg/g.

A preferred method of producing tobacco having a reduced amount of nicotine and TSNAs, involves genetic engineering directed at reducing the levels of nicotine and/or nornicotine or other alkaloids. Any enzyme involved in the nicotine synthesis pathway can be a suitable target for genetic engineering to reduce levels of nicotine and, optionally, levels of other alkaloids including nornicotine. Suitable targets for genetic engineering to produce tobacco having a reduced amount of nicotine and/or nitrosamines, especially TSNAs, include but are not limited to putrescine N-methyltransferase, N-methylputrescine oxidase, ornithine decarboxylase, S-adenosylmethionine synthetase, NADH dehydrogenase, phosphoribosylanthranilate isomerase or quinolate phosphoribosyl transferase (QPTase). Additionally, enzymes that regulate the flow of precursors into the nicotine synthesis pathway are suitable targets for genetic engineering to produce tobacco with a reduced amount of nicotine and nitrosamines, especially TSNAs. Suitable methods of genetic engineering are known in the art and include, for example, the use of antisense and sense suppression technology to reduce enzyme production, as well as use of random or targeted mutagenesis to disrupt gene function, for example, using T-DNA insertion or EMS mutagenesis.

By way of example, tobacco having reduced amounts of nicotine and TSNAs is generated from a tobacco plant that is created by exposing at least one tobacco cell of a selected tobacco variety (preferably Burley 21) to an exogenous DNA construct having, in the 5' to 3' direction, a promoter operable in a plant cell and DNA containing a portion of a DNA sequence that encodes an enzyme in the nicotine synthesis pathway or a complement thereof. The DNA is operably associated with said promoter and the tobacco cell is transformed with the DNA construct. The transformed cells are selected using either negative selection or positive selection techniques and at least one tobacco plant is regenerated from transformed cells. The regenerated tobacco plant or portion thereof is preferably analyzed to determine the amount of nicotine and/or TSNAs present and these values can be compared to the amount of nicotine and/or TSNAs present in a control tobacco plant or portion, preferably of the same variety.

The DNA constructs having a portion of a DNA sequence that encodes an enzyme in the nicotine synthesis pathway may have the entire coding sequence of the enzyme a complement of this sequence, or any portion thereof. A portion of a DNA sequence that encodes an enzyme in the nicotine synthesis pathway or the complement thereof may have at least 25, or preferably 50, or 75, or 100, or 150, or 250, or 500, or 750, or 1000, or 1500, or 2000, or 2500, or 5000, or the entire coding sequence of the enzyme or complement thereof. Accordingly, these DNA constructs have the ability to perturb the production of endogenous enzyme in the nicotine biosynthesis pathway through either an antisense or cosuppression mechanism. It is contemplated that both antisense and cosuppression constructs are effective at reducing the levels of nicotine and/or nitrosamines in tobacco plants.

In a preferred embodiment, the enzyme involved in the nicotine synthesis pathway can be, for example, putrescine N-methyltransferase, N-methylputrescine oxidase, ornithine decarboxylase, S-adenosylmethionine synthetase, NADH dehydrogenase, phosphoribosylanthranilate isomerase, or quinolate phosphoribosyl transferase (QPTase). In a preferred embodiment, the enzyme is QPTase. The segment of DNA sequence encoding an enzyme in the nicotine synthesis pathway may be in the antisense or the sense orientation. In a particularly preferred embodiment, the enzyme is QPTase.

By one approach, a novel cDNA sequence (SEQ ID NO: 1) encoding a plant quinolate phosphoribosyl transferase (QPTase) of SEQ ID NO: 2 is used. As QPTase activity is strictly correlated with nicotine content, construction of transgenic tobacco plants in which QPTase levels are lowered in the plant roots (compared to levels in wild-type plants) result in plants having reduced levels of nicotine in the leaves. Embodiments of the invention provide methods and nucleic acid constructs for producing such transgenic plants, as well as, the transgenic plants themselves. Such methods include the expression of antisense NtQPT1 RNA, which lowers the amount of QPTase in tobacco roots.

Aspects of the present invention also concern sense and antisense recombinant DNA molecules encoding QPTase or QPTase antisense RNA molecules, and vectors comprising those recombinant DNA molecules, as well as transgenic plant cells and plants transformed with those DNA molecules and vectors. Transgenic tobacco cells and the plants described herein are characterized in that they have a reduced amount of nicotine and/or TSNA as compared to unmodified or control tobacco cells and plants.

The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco and chewing tobacco in any form including leaf tobacco, shredded tobacco or cut tobacco. It is also contemplated that the low nicotine and/or TSNA tobacco described herein can be processed and blended with conventional tobacco so as to create a wide-range of tobacco products with varying amounts of nicotine and/or nitrosamines. These blended tobacco products can be used in tobacco product cessation programs so as to slowly move a consumer from a high nicotine and TSNA product to a low nicotine and TSNA product. Some embodiments of the invention comprise a tobacco use cessation kit, comprising two or more tobacco products with different levels of nicotine and/or nitrosamines. For example, a smoker can begin the program smoking blended cigarettes having 5 mg of nicotine and 0.3 μg of nitrosamine, gradually move to smoking cigarettes with 3 mg of nicotine and 0.2 μg of nitrosamine, followed by cigarettes having 2 mg nicotine and 0.1 μg nitrosamine, followed by cigarettes having 1.0 mg nicotine and 0.05 μg nitrosamine, followed by cigarettes having 0.05 mg nicotine and no detectable TSNA until the consumer decides to smoke only the cigarettes having virtually no nicotine and nitrosamines or quitting smoking altogether. Accordingly, the blended cigarettes described herein provide the basis for an approach to reduce the carcinogenic potential in a human in a step-wise fashion. The components of the tobacco use cessation kit described herein may include other tobacco products, including but not limited to, smoking materials (e.g., cigarettes, cigars, pipe tobacco), snuff, chewing tobacco, gum, and lozenges.

The present inventors have discovered that the TobRD2 gene (see Conkling et al., Plant Phys. 93, 1203 (1990)) encodes a *Nicotiana tabacum* QPTase, and provide herein the cDNA sequence of NtQPT1 (formerly termed TobRD2) and the amino acid sequence of the encoded enzyme. Aspects of the technology described herein are also described in PCT/US98/11893, which is hereby expressly incorporated by reference in its entirety. Comparisons of the NtQPT1 amino acid sequence with the GenBank database reveal limited sequence similarity to bacterial proteins that encode quinolate phosphoribosyl transferase (QPTase) (FIG. 3).

Quinolate phosphoribosyl transferase is required for de novo nicotine adenine dinucleotide (NAD) biosynthesis in both prokaryotes and eukaryotes. In tobacco, high levels of QPTase are detected in roots, but not in leaves. To determine that NtQPT1 encoded QPTase, the present inventors utilized *Escherichia coli* bacterial strain (TH265), a mutant lacking in quinolate phosphoribosyl transferase (nadC). This mutant cannot grow on minimal medium lacking nicotinic acid. However, expression of the NtQPT1 protein in this bacterial strain conferred the NadC+ phenotype (FIG. 4), confirming that NtQPT1 encodes QPTase.

Figure 5:
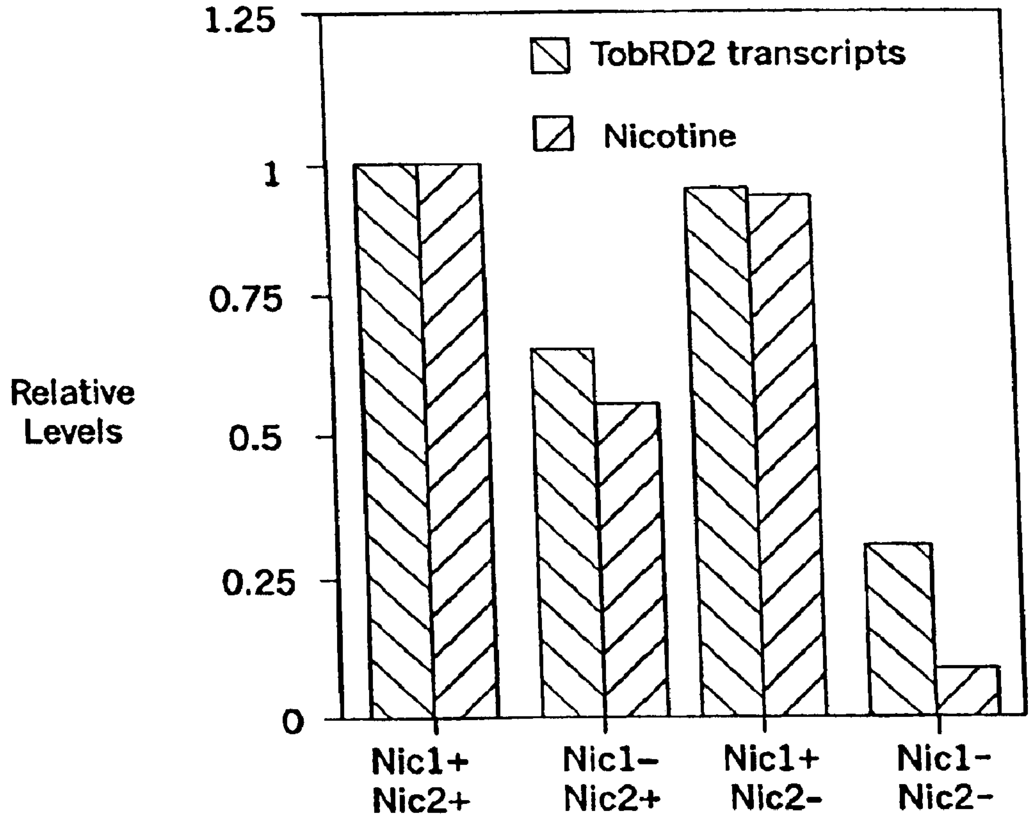
FIG. 5 compares nicotine levels and the relative steady-state NtQTP1 mRNA levels in Nic1 and Nic2 tobacco mutants; wild-type Burley 21 (Nic1/Nic1 Nic2/Nic2); Nic1-Burley 21 (nic1/nic1 Nic2/Nic2); Nic2-Burley 21 (Nic1/Nic1 nic2/nic2); and Nic1-Nic2-Burley 21 (nic1/nic1 nic2/Nnc2). Hatched bars, sloping downward and right indicate mRNA transcript levels; hatched bars, sloping downward and left indicate nicotine levels.

The effects of Nic1 and Nic2 mutants in tobacco, and the effects of topping tobacco plants, on NtQPT1 steady-state mRNA levels and nicotine levels were determined. (Removal of apical dominance by topping at onset of flowering is well known to result in increased levels of nicotine biosynthesis and transport in tobacco, and is a standard practice in tobacco production.) If NTQPT1 is in fact involved in nicotine biosynthesis, it would be expected that (1) NtQPT1 mRNA levels would be lower in nic1/nic2 double mutants and (2) NtQPT1 mRNA levels would increase after topping. NtQPT1 mRNA levels in nic1/nic2 double mutants were found to be approximately 25% that of wild-type (FIG. 5). Further, within six hours of topping, the NtQPT1 mRNA levels in tobacco plants increased about eight-fold. Therefore, NtQPT1 was determined to be a key regulatory gene in the nicotine biosynthetic pathway. The next section describes the creation of transgenic tobacco plant cells and transgenic tobacco plants.

Transgenic Plant Cells and Plants

Regulation of gene expression in plant cell genomes can be achieved by integration of heterologous DNA under the transcriptional control of a promoter which is functional in the host, and in which the transcribed strand of heterologous DNA is complementary to the strand of DNA that is transcribed from the endogenous gene to be regulated. The introduced DNA, referred to as antisense DNA, provides an RNA sequence which is complementary to naturally produced (endogenous) mRNAs and which inhibits expression of the endogenous mRNA. Although the mechanism of antisense is not completely understood, it is known that antisense constructs can be used to regulate gene expression.

In some methods of the invention, the antisense product may be complementary to coding or non-coding (or both)

portions of naturally occurring target RNA. The antisense construction may be introduced into the plant cells in any suitable manner, and may be integrated into the plant genome for inducible or constitutive transcription of the antisense sequence.

As used herein, exogenous or heterologous DNA (or RNA) refers to DNA (or RNA) that has been introduced into a cell (or the cell's ancestor) through the efforts of humans. Such heterologous DNA may be a copy of a sequence which is naturally found in the cell being transformed, or fragments thereof. To produce a tobacco plant having decreased QPTase levels, and a reduced amount of nicotine and TSNAs, as compared to an untransformed or control tobacco plant or portion thereof, a tobacco cell may be transformed with an exogenous QPT antisense transcriptional unit comprising a partial QPT cDNA sequence, a full-length QPT cDNA sequence, a partial QPT chromosomal sequence, or a full-length QPT chromosomal sequence, in the antisense orientation with appropriate operably linked regulatory sequences. Appropriate regulatory sequences include a transcription initiation sequence ("promoter") operable in the plant being transformed, and a polyadenylation/transcription termination sequence. Standard techniques, such as restriction mapping, Southern blot hybridization, and nucleotide sequence analysis, are then employed to identify clones bearing QPTase sequences in the antisense orientation, operably linked to the regulatory sequences.

Tobacco plants are then regenerated from successfully transformed cells using conventional techniques. It is most preferred that the antisense sequence utilized be complementary to the endogenous sequence, however, minor variations in the exogenous and endogenous sequences may be tolerated. It is preferred that the antisense DNA sequence be of sufficient sequence similarity to the extent that it is capable of binding to the endogenous sequence in the cell to be regulated, under stringent conditions as described below.

Antisense technology has been employed in several laboratories to create transgenic plants characterized by lower than normal amounts of specific enzymes. For example, plants with lowered levels of chalcone synthase, an enzyme of a flower pigment biosynthetic pathway, have been produced by inserting a chalcone synthase antisense gene into the genome of tobacco and petunia. These transgenic tobacco and petunia plants produce flowers with lighter than normal coloration (Van der Krol et al., "An Anti-Sense Chalcone Synthase Gene in Transgenic Plants Inhibits Flower Pigmentation", Nature, 333, pp. 866–69 (1988)). Antisense RNA technology has also been successfully employed to inhibit production of the enzyme polygalacturonase in tomatoes (Smith et al., "Antisense RNA Inhibition of Polygalacturonase Gene Expression in Transgenic Tomatoes", Nature, 334, pp. 724–26 (1988); Sheehy et al., "Reduction of Polygalacturonase Activity in Tomato Fruit by Antisense RNA", Proc. NM. Acad SU USA, 85, pp. 8805–09 (1988)), and the small subunit of the enzyme ribulose bisphosphate carboxylase in tobacco (Rodermel et al., "Nuclear-Organelle Interactions: Nuclear Antisense Gene Inhibits Ribulose Bisphosphate Carboxylase Enzyme Levels in Transformed Tobacco Plants", Cell, 55, pp. 673–81 (1988)).

Alternatively, transgenic plants characterized by greater than normal amounts of a given enzyme may be created by transforming the plants with the gene for that enzyme in the sense (i.e., normal) orientation. Levels of nicotine in the transgenic tobacco plants of the present invention can be detected by standard nicotine assays. Transformed plants in which the level of QPTase is reduced compared to untransformed control plants will accordingly have a reduced nicotine level compared to the control; transformed plants in which the level of QPTase is increased compared to untransformed control plants will accordingly have an increased nicotine level compared to the control.

The heterologous sequence utilized in the antisense methods of the present invention may be selected so as to produce an RNA product complementary to the entire QPTase mRNA sequence, or to a portion thereof. The sequence may be complementary to any contiguous sequence of the natural messenger RNA, that is, it may be complementary to the endogenous mRNA sequence proximal to the 5'-terminus or capping site, downstream from the capping site, between the capping site and the initiation codon and may cover all or only a portion of the non-coding region, may bridge the non-coding and coding region, be complementary to all or part of the coding region, complementary to the C-terminus of the coding region, or complementary to the 3'-untranslated region of the mRNA. Suitable antisense sequences may be from at least about 13 to about 15 nucleotides, at least about 16 to about 21 nucleotides, at least about 20 nucleotides, at least about 30 nucleotides, at least about 50 nucleotides, at least about 75 nucleotides, at least about 100 nucleotides, at least about 125 nucleotides, at least about 150 nucleotides, at least about 200 nucleotides, or more. In addition, the sequences may be extended or shortened on the 3' or 5' ends thereof.

The particular anti-sense sequence and the length of the anti-sense sequence will vary depending upon the degree of inhibition desired, the stability of the anti-sense sequence and the like. One of skill in the art will be guided in the selection of appropriate QPTase antisense sequences using techniques available in the art and the information provided herein. With reference to FIG. 2A and SEQ ID NO: 1 herein, an oligonucleotide of the invention may be a continuous fragment of the QPTase cDNA sequence in antisense orientation, of any length that is sufficient to achieve the desired effects when transformed into a recipient plant cell.

The present invention may also be used in methods of sense co-suppression of nicotine production. Sense DNAs employed in carrying out the present invention are of a length sufficient to, when expressed in a plant cell, suppress the native expression of the plant QPTase protein as described herein in that plant cell. Such sense DNAs may be essentially an entire genomic or complementary DNA encoding the QPTase enzyme, or a fragment thereof, with such fragments typically being at least 15 nucleotides in length. Methods of ascertaining the length of sense DNA that results in suppression of the expression of a native gene in a cell are available to those skilled in the art.

In an alternate embodiment of the present invention, *Nicotiana* plant cells are transformed with a DNA construct containing a DNA segment encoding an enzymatic RNA molecule (i.e., a "ribozyme"), which enzymatic RNA molecule is directed against (i.e., cleaves) the mRNA transcript of DNA encoding plant QPTase as described herein. Ribozymes contain substrate binding domains that bind to accessible regions of the target mRNA, and domains that catalyze the cleavage of RNA, preventing translation and protein production. The binding domains may comprise antisense sequences complementary to the target mRNA sequence; the catalytic motif may be a hammerhead motif or other motifs, such as the hairpin motif. Ribozyme cleavage sites within an RNA target may initially be identified by scanning the target molecule for ribozyme cleavage sites (e.g., GUA, GUU or GUC sequences). Once identified, short RNA sequences of 15, 20, 30 or more ribonucleotides corresponding to the region of the target gene containing the cleavage site may be evaluated for predicted structural features. The suitability of candidate targets may also be evaluated by testing their accessibility to hybridization with complimentary oligonucleotides, using ribonuclease protection assays as are known in the art. DNA sequences encoding enzymatic RNA molecules may be produced in accordance with known techniques. See, e.g., T. Cech et al., U.S. Pat. No. 4,987,071; Keene et al., U.S. Pat. No. 5,559,021; Donson et al., U.S. Pat. No. 5,589,367; Torrence et al., U.S. Pat. No. 5,583,032; Joyce, U.S. Pat. No. 5,580,967; Gold et al. U.S. Pat. No. 5,595,877; Wagner et al., U.S. Pat. No. 5,591,601; and U.S. Pat. No. 5,622,854 (the disclosures of which are to be incorporated herein by reference in their entirety).

Production of such an enzymatic RNA molecule in a plant cell and disruption of QPTase protein production reduces QPTase activity in plant cells in essentially the same manner as production of an antisense RNA molecule: that is, by disrupting translation of mRNA in the cell which produces the enzyme. The term ‘ribozyme’ is used herein to describe an RNA-containing nucleic acid that functions as an enzyme (such as an endoribonuclease), and may be used interchangeably with ‘enzymatic RNA molecule’. The present invention further includes DNA encoding the ribozymes, DNA encoding the ribozymes that has been inserted into an expression vector, host cells containing such vectors and methods of decreasing QPTase production in plants using ribozymes.

Nucleic acid sequences employed in carrying out the present invention include those with sequence similarity to SEQ ID NO: 1, and encoding a protein having quinolate phosphoribosyl transferase activity. This definition is intended to encompass natural allelic variations in QPTase proteins. Thus, DNA sequences that hybridize to DNA of SEQ ID NO: 1 and code for expression of QPTase, particularly plant QPTase enzymes, may also be employed in carrying out the present invention. Multiple forms of the tobacco QPT enzyme may exist. Multiple forms of an enzyme may be due to post-translational modification of a single gene product, or to multiple forms of the NtQPT1 gene.

Conditions which permit other DNA sequences which code for expression of a protein having QPTase activity to hybridize to DNA of SEQ ID NO: 1 or to other DNA sequences encoding the protein given as SEQ ID NO: 2 can be determined in a routine manner. For example, hybridization of such sequences to DNA encoding the protein given as SEQ ID NO: 2 may be carried out under conditions of reduced stringency or even stringent conditions (e.g., conditions represented by a wash stringency of 0.3 M NaCl, 0.03 M sodium citrate, 0.1% SDS at 60° C. or even 70° C.) herein in a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar or more, with the sequence given herein as SEQ ID NO: 1, or DNA sequences encoding proteins of SEQ ID NO: 2. (Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.)

Differential hybridization procedures are available which allow for the isolation of cDNA clones whose mRNA levels are as low as about 0.05% of poly(A)RNA. See M. Conkling et al., Plant Physiol. 93, 1203–1211 (1990). In brief, cDNA libraries are screened using single-stranded cDNA probes of reverse transcribed mRNA from plant tissue (e.g., roots and/or leaves). For differential screening, a nitrocellulose or nylon membrane is soaked in 5×SSC and placed in a 96 well suction manifold; 150 $\mu$L of stationary overnight culture is transferred from a master plate to each well and vacuum applied until all liquid has passed through the filter. Approximately, 150 $\mu$L of denaturing solution (0.5M NaOH, 1.5 M NaCl) is placed in each well using a multiple pipetter and allowed to sit about 3 minutes. Suction is applied as above and the filter removed and neutralized in 0.5 M Tris-HCl (pH 8.0), 1.5 M NaCl. It is then baked 2 hours in vacuo and incubated with the relevant probes. By using nylon membrane filters and keeping master plates stored at −70° C. in 7% DMSO, filters may be screened multiple times with multiple probes and appropriate clones recovered after several years of storage.

As used herein, the term ‘gene’ refers to a DNA sequence that incorporates (1) upstream (5') regulatory signals including the promoter, (2) a coding region specifying the product, protein or RNA of the gene, (3) downstream regions including transcription termination and polyadenylation signals and (4) associated sequences required for efficient and specific expression. The DNA sequence of the present invention may consist essentially of the sequence provided herein (SEQ ID NO: 1), or equivalent nucleotide sequences representing alleles or polymorphic variants of these genes, or coding regions thereof. Use of the phrase “substantial sequence similarity” in the present specification and claims means that DNA, RNA or amino acid sequences which have slight and non-consequential sequence variations from the actual sequences disclosed and claimed herein are considered to be equivalent to the sequences of the present invention. In this regard, “slight and non-consequential sequence variations” mean that “similar” sequences (i.e., the sequences that have substantial sequence similarity with the DNA, RNA or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

DNA sequences provided herein can be transformed into a variety of host cells. A variety of suitable host cells, having desirable growth and handling properties, are readily available in the art. Use of the phrase “isolated” or “substantially pure” in the present specification and claims as a modifier of DNA, RNA, polypeptides or proteins means that the DNA, RNA, polypeptides or proteins so designated have been separated from their in vivo cellular environments through the efforts of human beings.

As used herein, a “native DNA sequence” or “natural DNA sequence” means a DNA sequence that can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art. As used herein, a native plant DNA sequence is that which can be isolated from non-transgenic plant cells or tissue. As used herein, a native tobacco DNA sequence is that which can be isolated from non-transgenic tobacco cells or tissue.

DNA constructs, or “transcription cassettes,” of the present invention include, 5' to 3' in the direction of transcription, a promoter as discussed herein, a DNA sequence as discussed herein operatively associated with the promoter, and, optionally, a termination sequence including stop signal for RNA polymerase and a polyadenylation signal. All of these regulatory regions should be capable of operating in the cells of the tissue to be transformed. Any suitable termination signal may be employed in carrying out the present invention, examples thereof including, but not limited to, the nopaline synthase (nos) terminator, the octapine synthase (ocs) terminator, the CaMV terminator or native termination signals, derived from the same gene as the transcriptional initiation region or derived from a different gene. See, e.g., Rezian et al. (1988) supra, and Rodermel et al. (1988), supra.

The term "operatively associated," as used herein, refers to DNA sequences on a single DNA molecule that are associated so that the function of one sequence is affected by the other. Thus, a promoter is operatively associated with a DNA when it is capable of affecting the transcription of that DNA (i.e., the DNA is under the transcriptional control of the promoter). The promoter is said to be "upstream" from the transcribed DNA sequence, which is in turn said to be "downstream" from the promoter.

The transcription cassette may be provided in a DNA construct that also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide (such as antibiotics, toxins, heavy metals or the like), provide complementation by imparting prototrophy to an auxotrophic host and/or provide a visible phenotype through the production of a novel compound in the plant.

The various fragments comprising the various constructs, transcription cassettes, markers and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature as demonstrated by J. Sambrook et al., Molecular Cloning, A Laboratory Manual (2d Ed. 1989) (Cold Spring Harbor Laboratory).

Vectors that may be used to transform plant tissue with nucleic acid constructs of the present invention include both *Agrobacterium* vectors and ballistic vectors, as well as vectors suitable for DNA-mediated transformation. The term 'promoter' refers to a region of a DNA sequence that incorporates the necessary signals for the efficient expression of a coding sequence. This may include sequences to which an RNA polymerase binds, but is not limited to such sequences, and may include regions to which other regulatory proteins bind along with regions involved in the control of protein translation. They may also include coding sequences.

Promoters employed in carrying out the invention may be constitutively active promoters. Numerous constitutively active promoters that are operable in plants are available. A preferred example is the Cauliflower Mosaic Virus (CaMV) 35S promoter, which is expressed constitutively in most plant tissues. As an alternative, the promoter may be a root-specific promoter or root cortex specific promoter, as explained in greater detail below.

Antisense sequences have been expressed in transgenic tobacco plants utilizing the Cauliflower Mosaic Virus (CaMV) 35S promoter. See, e.g., Cornelissen et al., "Both RNA Level and Translation Efficiency are Reduced by Anti-Sense RNA in Transgenic Tobacco", Nucleic Acids Res. 17, pp. 833–43 (1989); Rezaian et al., "Anti-Sense RNAs of Cucumber Mosaic Virus in Transgenic Plants Assessed for Control of the Virus", Plant Molecular Biology 11, pp. 463–71 (1988); Rodermel et al., "Nuclear-Organelle Interactions: Nuclear Antisense Gene Inhibits Ribulose Bisphosphate Carboxylase Enzyme Levels in Transformed Tobacco Plants", Cell 55, pp. 673–81 (1988); Smith et al., "Antisense RNA Inhibition of Polygalacturonase Gene Expression in Transgenic Tomatoes", Nature 334, pp. 724–26 (1988); Van der Krol et al., "An Anti-Sense Chalcone Synthase Gene in Transgenic Plants Inhibits Flower Pigmentation", Nature 333, pp. 866–69 (1988).

Use of the CaMV $^{35}$S promoter for expression of QPTase in the transformed tobacco cells and plants of this invention is preferred. Use of the CaMV promoter for expression of other recombinant genes in tobacco roots has been well described (Lam et al., "Site-Specific Mutations Alter In Vitro Factor Binding and Change Promoter Expression Pattern in Transgenic Plants", Proc. Nat. Acad. Sci. USA 86, pp. 7890–94 (1989); Poulsen et al. "Dissection of 5' Upstream Sequences for Selective Expression of the *Nicotiana plumbaginifolia* rbcS-8B Gene", Mol. Gen. Genet. 214, pp. 16–23 (1988)).

Other promoters that are active only in root tissues (root specific promoters) are also particularly suited to the methods of the present invention. See, e.g., U.S. Pat. No. 5,459,252 to Conkling et al.; Yamamoto et al., The Plant Cell, 3:371 (1991). The TobRD2 root-cortex specific promoter may also be utilized. See, eg., U.S. patent application Ser. No. 08/508,786, now allowed, to Conkling et al; PCT WO 9705261. All patents cited herein are intended to be incorporated herein by reference in their entirety.

The QPTase recombinant DNA molecules and vectors used to produce the transformed tobacco cells and plants of this invention may further comprise a dominant selectable marker gene. Suitable dominant selectable markers for use in tobacco include, inter alia, antibiotic resistance genes encoding neomycin phosphotransferase (NPTII) and hygromycin phosphotransferase (HPT). Other well-known selectable markers that are suitable for use in tobacco include a mutant dihydrofolate reductase gene that encodes methotrexate-resistant dihydrofolate reductase. DNA vectors containing suitable antibiotic resistance genes, and the corresponding antibiotics, are commercially available.

Transformed tobacco cells are selected out of the surrounding population of non-transformed cells by placing the mixed population of cells into a culture medium containing an appropriate concentration of the antibiotic (or other compound normally toxic to tobacco cells) against which the chosen dominant selectable marker gene product confers resistance. Thus, only those tobacco cells that have been transformed will survive and multiply. Additionally, the positive selection techniques described by Jefferson (e.g., WO 00055333; WO 09913085; U.S. Pat. Nos. 5,599,670; 5,432,081; and 5,268,463, hereby expressly incorporated by reference in their entireties) can be used.

Methods of making recombinant plants of the present invention, in general, involve first providing a plant cell capable of regeneration (the plant cell typically residing in a tissue capable of regeneration). The plant cell is then transformed with a DNA construct comprising a transcription cassette of the present invention (as described herein) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the transcription cassette or any other technique suitable for the production of a transgenic plant.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention.

Microparticles suitable for the ballistic transformation of a plant cell, carrying a DNA construct of the present invention, are also useful for making the transformed plants described herein. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580. When using ballistic transformation procedures, the transcription cassette may be incorporated into a plasmid capable of replicating in or integrating into the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts. Plants may be subsequently regenerated from the transformed protoplasts in accordance with procedures well known in the art. Fusion of tobacco protoplasts with DNA-containing liposomes or with DNA constructs via electroporation is known in the art. (Shillito et al., "Direct Gene Transfer to Protoplasts of Dicotyledonous and Monocotyledonous Plants by a Number of Methods, Including Electroporation", Methods in Enzymology 153, pp. 313–36 (1987)).

As used herein, transformation refers to the introduction of exogenous DNA into cells so as to produce transgenic cells stably transformed with the exogenous DNA. Transformed cells are induced to regenerate intact tobacco plants through application of tobacco cell and tissue culture techniques that are well known in the art. The method of plant regeneration is chosen so as to be compatible with the method of transformation. The stable presence and the orientation of the QPTase sequence in transgenic tobacco plants can be verified by Mendelian inheritance of the QPTase sequence, as revealed by standard methods of DNA analysis applied to progeny resulting from controlled crosses. After regeneration of transgenic tobacco plants from transformed cells, the introduced DNA sequence is readily transferred to other tobacco varieties through conventional plant breeding practices and without undue experimentation.

For example, to analyze the segregation of the transgene, regenerated transformed plants (RO) may be grown to maturity, tested for nicotine and/or TSNA levels, and selfed to produce $R_1$ plants. A percentage of $R_1$ plants carrying the transgene are homozygous for the transgene. To identify homozygous $R_1$ plants, transgenic $R_1$ plants are grown to maturity and selfed. Homozygous $R_1$ plants will produce $R_2$ progeny where each progeny plant carries the transgene; progeny of heterozygous $R_1$, plants will segregate 3:1.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems) and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or $T_1$) transformed plants may be selfed to give homozygous second generation (or $T_2$) transformed plants and the $T_2$ plants further propagated through classical breeding techniques. A dominant selectable marker (such as nptII) can be associated with the transcription cassette to assist in breeding.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having lowered QPTase activity and thus having decreased nicotine and/or TSNA levels, as compared to a similar crop of non-transformed plants of the same species and variety. The examples that follow are set forth to illustrate the present invention, and are not to be construed as limiting thereof.

EXAMPLE 1

Isolation and Sequencing

TobRD2 cDNA (Conkling et. al., Plant Phys. 93, 1203 (1990)) was sequenced and is provided herein as SEQ ID NO: 1, and the deduced amino acid sequence as SEQ ID NO: 2. The deduced amino acid sequence was predicted to be a cytosolic protein. Although plant QPTase genes had not yet been reported, comparisons of the NtPT1 amino acid sequence with the GenBank database (FIG. 3) revealed limited sequence similarity to certain bacterial and other proteins; quinolate phosphoribosyl transferase (QPTase) activity has been demonstrated for the *S. typhimurium, E. coli*, and *N. tabacum* genes. The NtQPT1-encoded QPTase has similarity to the deduced peptide fragment encoded by an Arabidopsis EST (expression sequence tag) sequence (Genbank Accession number F20096), which may represent part of an *Arabidopsis* QPTase gene.

EXAMPLE 2

In-Situ Hybridization

To determine the spatial distribution of TobRD2 mRNA transcripts in the various tissues of the root, in situ hybridizations were performed in untransformed plants. In-situ hybridizations of the antisense strand of TobRD2 to the TobRD2 mRNA in root tissue was done using techniques as described in Meyerowitz, *Plant Mol. Biol. Rep.* 5:242 (1987) and Smith et al., *Plant Mol. Biol. Rep.* 5:237 (1987). Seven day old tobacco (*Nicotania tabacum* L.) seedling roots were fixed in phosphate-buffered glutaraldehyde, embedded in Paraplast Plus (Monoject Inc., St. Louis, Mo.) and sectioned at 8 micron thickness to obtain transverse as well as longitudinal sections. Antisense TobRD2 transcripts, synthesized In vitro in the presence of $^{35}$S-ATP, were used as probes. The labeled RNA was hydrolyzed by alkaline treatment to yield 100 to 200 base mass average length prior to use.

Hybridizations were done in 50% formamide for 16 hours at 42° C., with approximately $5\times10^6$ counts-per-minute (cpm)-labeled RNA per milliliter of hybridization solution. After exposure, the slides were developed and visualized under bright and dark field microscopy.

The hybridization signal was localized to the cortical layer of cells in the roots. Comparison of both bright and dark field images of the same sections localized TobRD2 transcripts to the parenchymatous cells of the root cortex. No hybridization signal was visible in the epidermis or the stele.

EXAMPLE 3

TobRD2 mRNA Levels in Nic1 and Nic2 Tobacco Mutants and Correlation to Nicotine Levels TobRD2 steady-state mRNA levels were examined in Nic1 and Nic2 mutant tobacco plants. Nic1 and Nic2 are known to regulate quinolate phosphoribosyl. transferase activity and putrescence methyl-transferase activity, and are co-dominant regulators of nicotine production. The present results are illustrated in FIGS. 5A and 5B and show that TobRD2 expression is regulated by Nic1 and Nic 2.

RNA was isolated from the roots of wild-type Burley 21 tobacco plants (Nic1/Nic1 Nic2/Nic2), roots of Nic1-Burley 21 (nic1/nic1 Nic2/Nic2), roots of Nic2-Burley 21 (Nic1/Nic1 nic2/nic2) and roots of Nic1/Nic2-Burley 21 (nic1/nic1 nic2/nic2).

Four Burley 21 tobacco lines were grown from seed in soil for a month and transferred to hydroponic chambers in aerated nutrient solution in a greenhouse for one month. These lines were isogenic, except for the two low-nicotine loci, and had genotypes of Nic1/Nic1 Nic2/Nic2; nic1/nic1 Nic2/Nic2; Nic1/Nic1 nic2/nic2; nic1/nic1 nic2/nic2. Roots were harvested from about 20 plants for each genotype and pooled for RNA isolation. Total RNA (1 $\mu$g) from each genotype was electrophoresed through a 1% agarose gel containing 1.1M formaldehyde and transferred to a nylon membrane according to Sambrook et al. (1989). The membranes were hybridized with IP-labeled TobRD2 cDNA fragments. Relative intensity of TobRD2 transcripts were measured by densitometry. FIG. 5 (solid bars) illustrates the relative transcript levels (compared to Nic1/Nic1 Nic2/Nic2) for each of the four genotypes. The relative nicotine content (compared to Nic1/Nic1 Nic2/Nic2) of the four genotypes is shown by the hatched bars.

FIG. 5 graphically compares the relative steady state TobRD2 mRNA level, using the level found in wild-type Burley 21 (Nic1/Nic1 Nic2/Nic2) as the reference amount. TobRD2 mRNA levels in nic1/nic1 nic2/nic2 double mutants were approximately 25% that of wild-type tobacco. FIG. 5B further compares the relative levels of nicotine in the near isogenic lines of tobacco studied in this example (solid bars indicate TobRD2 transcript level; hatched bars indicate nicotine level). There was a close correlation between nicotine levels and TobRD2 transcript levels.

EXAMPLE 4

Complementation of Bacterial Mutant Lacking QPTase with DNA of SEQ ID NO: 1

*Escherichia coli* strain TH265 is a mutant lacking quinolate phosphoribosyl transferase (nadC−), and therefore cannot grow on media lacking nicotinic acids. TH265 cells were transformed with an expression vector (pWS161) containing DNA of SEQ ID NO: 1, or transformed with the expression vector (pKK233) only. Growth of the transformed bacteria was compared to growth of TH265 (pKK233) transformants, and to growth of the untransformed TH265 nadC− mutant. Growth was compared on ME minimal media (lacking nicotinic acid) and on ME minimal media with added nicotinic acid.

The *E. coli* strain with the QPTase mutation (nadC), TH265, was kindly provided by Dr. K. T. Hughes (Hughes et al., J Bact. 175:479 (1993). The cells were maintained on LB media and competent cells prepared as described in Sambrook et al (1989). An expression plasmid was constructed in pKK2233 (Brosius, 1984) with the TobRD2 cDNA cloned under the control of the Tac promoter. The resulting plasmid, pWS161, was transformed into TH265 cells. The transformed cells were then plated on minimal media (Vogel and Bonner, 1956) agar plates with or without nicotinic acid (0.0002%) as supplement. TH265 cells alone and TH265 transformed with pKK2233 were plated on similar plates for use as controls.

Figure 4:
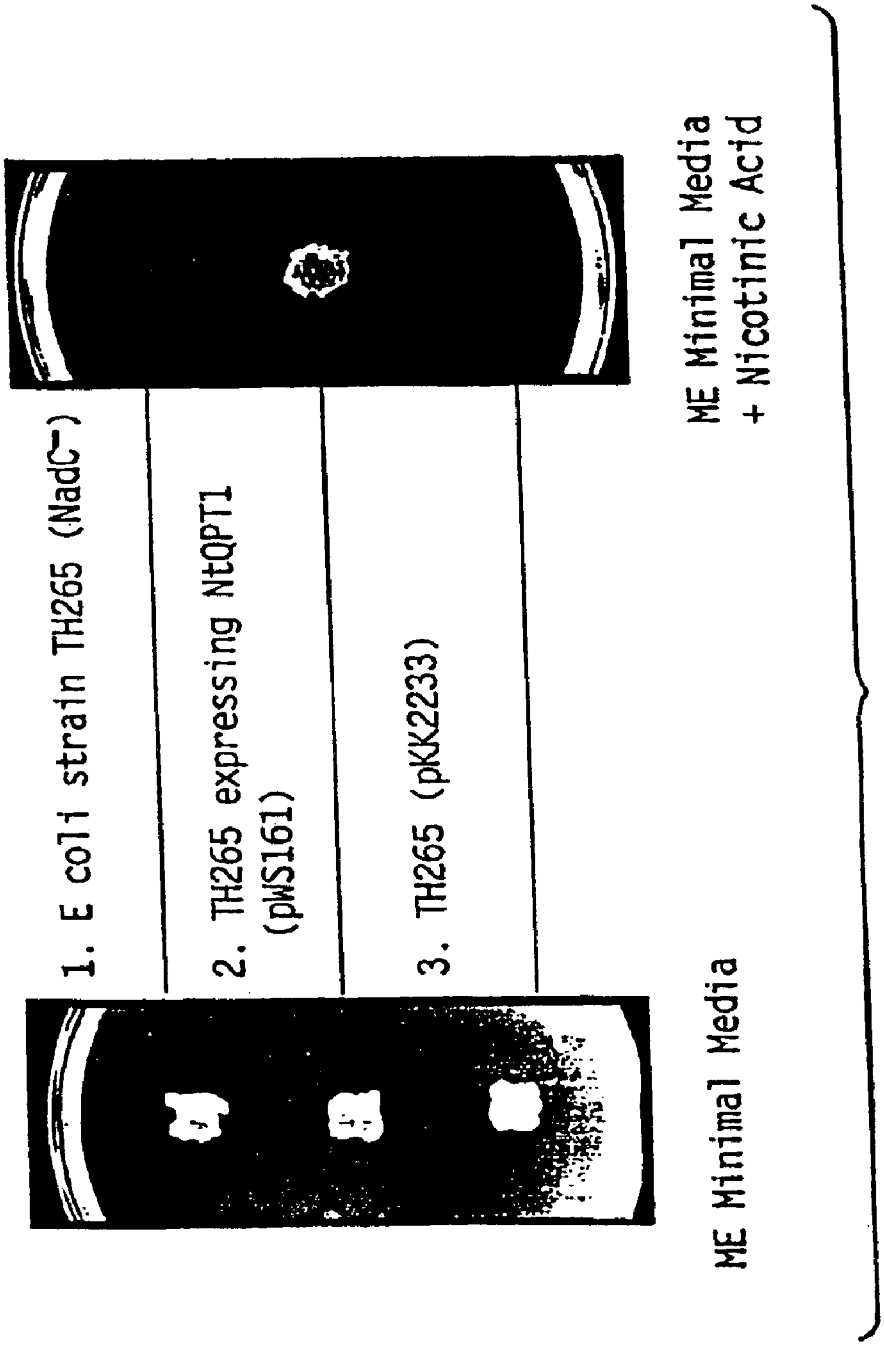
FIG. 4 shows the results of complementation of an *Escherichia coli* mutant lacking quinolate phosphoribosyl transferase (TH265) with NtQPT1 cDNA. Cells were transformed with an expression vector carrying NtQPT 1; growth of transformed TH265 cells expressing NtQPT1 on minimal medium lacking nicotinic acid demonstrated that NtQPT1 encodes QPTase.

Results are shown in FIG. 4. Only the TH265 transformed with DNA of SEQ ID NO: 1 grew in media lacking nicotinic acid. These results show that expression of DNA of SEQ ID NO: 1 in TH265 bacterial cells conferred the NadC+ phenotype on these cells, confirming that this sequence encodes QPTase. The TobRD2 nomenclature was thus changed to NtQPT1.

EXAMPLE 5

Transformation of Tobacco Plants

DNA of SEQ ID NO: 1, in antisense orientation, is operably linked to a plant promoter (CaMV 35S or TobRD2 root-cortex specific promoter) to produce two different DNA cassettes: CaMV35S promoter/antisense SEQ ID NO: 1 and TobRD2 promoter/antisense SEQ ID NO: 1.

A wild-type tobacco line and a low-nicotine tobacco line are selected for transformation, e.g., wild-type Burley 21 tobacco (Nic1+/Nic2+) and homozygous Nic1−/Nic2− Burley 21. A plurality of tobacco plant cells from each line are transformed using each of the DNA cassettes. Transformation is conducted using an *Agrobacterium* vector, e.g., an Agrobacterium-binary vector carrying Ti-border sequences and the nptII gene (conferring resistance to kanamycin and under the control of the nos promoter (nptII)).

Transformed cells are selected and regenerated into transgenic tobacco plants called $R_o$. The $R_o$ plants are grown to maturity and tested for levels of nicotine; a subset of the transformed tobacco plants exhibit significantly lower levels of nicotine compared to non-transformed control plants.

$R_o$ plants are then selfed and the segregation of the transgene is analyzed in next generation, the $R_1$ progeny. $R_1$ progeny are grown to maturity and selfed; segregation of the transgene among $R_2$ progeny indicates which $R_1$ plants are homozygous for the transgene.

EXAMPLE 6

Tobacco Having Reduced Nicotine Levels

Tobacco of the variety Burley 21 LA was transformed with the binary *Agrobacterium* vector pYTY32 to produce a low nicotine tobacco variety, Vector 21–41. The binary vector pYTY32 carried the 2.0 kb NtQPT1 root-cortex-specific promoter driving antisense expression of the NtQPT1 cDNA and the nopaline synthase (nos) 3' termination sequences from *Agrobacterium tumefaciens* T-DNA. The selectable marker for this construct was neomycin phosphotransferase (nptII) from *E. coli* Tn5, which confers resistance to kanamycin; the expression of nptII was directed by the nos promoter from *Agrobacterium tumefaciens* T-DNA. Transformed cells, tissues and seedlings were selected by their ability to grow on Murashige-Skoog (MS) medium containing 300 μg/ml kanamycin. Burley 21 LA is a variety of Burley 21 with substantially reduced levels of nicotine as compared with Burley 21 (i.e., Burley 21 LA has 8% the nicotine levels of Burley 21, see Legg et al., *Can J Genet Cytol,* 13:287–91 (1971); Legg et al., *J Hered,* 60:213–17 (1969))

One hundred independent pYTY32 transformants of Burley 21 LA ($T_0$) were allowed to self. Progeny of the selfed plants ($T_1$) were germinated on medium containing kanamycin and the segregation of kanamycin resistance scored. $T_1$ progeny segregating 3:1 resulted from transformation at a single locus and were subjected to further analysis.

Nicotine levels of $T_1$ progeny segregating 3:1 were measured qualitatively using a micro-assay technique. Approximately 200 mg fresh tobacco leaves were collected and ground in 1 ml extraction solution (extraction solution: 1 ml Acetic acid in 100 ml $H_2O$). Homogenate was centrifuged for 5 min at 14,000×g and supernatant removed to a clean tube, to which the following reagents were added: 100 μL $NH_4OAC$ (5 g/100 ml $H_2O$+50 μL Brij 35); 500 μL Cyanogen Bromide (Sigma C-6388, 0.5 g/100 ml $H_2O$+50 μL Brij 35); 400 μL Aniline (0.3 ml buffered Aniline in 100 ml $NH_4OAC$+50 μL Brij 35). A nicotine standard stock solution of 10 mg/ml in extraction solution was prepared and diluted to create a standard series for calibration. Absorbance at 460 nm was read and nicotine content of test samples were determined using the standard calibration curve.

$T_1$ progeny that had less than 10% of the nicotine levels of the Burley 21 LA parent were allowed to self to produce $T_2$ progeny. Homozygous $T_2$ progeny were identified by germinating seeds on medium containing kanamycin and selecting clones in which 100% of the progeny were resistant to kanamycin (i.e., segregated 4:0; heterozygous progeny would segregate 3:1). Nicotine levels in homozygous and heterozygous $T_2$ progeny were qualitatively determined using the micro-assay and again showed levels less than 10% of the Burley 21 LA parent. Leaf samples of homozygous $T_2$ progeny were sent to the Southern Research and Testing Laboratory in Wilson, N.C. for quantitative analysis of nicotine levels using Gas Chromatography/Flame Ionization Detection (GC/FID). Homozygous $T_2$ progeny of transformant #41 gave the lowest nicotine levels (~70 ppm), and this transformant was designated as "Vector 21–41."

Vector 21–41 plants were allowed to self-cross, producing $T_3$ progeny. $T_3$ progeny were grown and nicotine levels assayed qualitatively and quantitatively. $T_3$ progeny were allowed to self-cross, producing $T_4$ progeny. Samples of the bulked seeds of the $T_4$ progeny were grown and nicotine levels tested.

In general, Vector 21–41 is similar to Burley 21 LA in all assessed characteristics, with the exception of alkaloid content and total reducing sugars (e.g., nicotine and nor-nicotine). Vector 21–41 may be distinguished from the parent Burley 21 LA by its substantially reduced content of nicotine, nor-nicotine and total alkaloids. As shown below, total alkaloid concentrations in Vector 21–41 are significantly reduced to approximately relative to the levels in the parent Burley 21 LA, and nicotine and nor-nicotine concentrations show dramatic reductions in Vector 21–41 as compared with Burley 21 LA. Vector 21–41 also has significantly higher levels of reducing sugars as compared with Burley 21 LA.

Field trials of Vector 21–41 $T_4$ progeny were performed at the Central Crops Research Station (Clayton, N.C.) and compared to the Burley 21 LA parent. The design was three treatments (Vector 21–41, a Burley 21 LA transformed line carrying only the NtQPT1 promoter [Promoter-Control], and untransformed Burley 21 LA [Wild-type]), 15 replicates, 10 plants per replicate. The following agronomic traits were measured and compared: days from transplant to flowering; height at flowering; leaf number at flowering; yield; percent nicotine; percent nor-nicotine; percent total nitrogen; and percent reducing sugars.

EXAMPLE 7

Low Nicotine and Nitrosamine Blended Tobacco

The following example describes several ways to create tobacco products having specific amounts of nicotine and/or TSNAs through blending. Some blending approaches begin with tobacco prepared from varieties that have extremely low amounts of nicotine and/or TSNAs. By blending prepared tobacco from a low nicotine/TSNA variety (e.g., undetectable levels of nicotine and/or TSNAs) with a conventional tobacco (e.g., Burley, which has 30,000 parts per million (ppm) nicotine and 8,000 parts per billion (ppb) TSNA; Flue-Cured, which has 20,000 ppm nicotine and 300 ppb TSNA; and Oriental, which has 10,000 ppm nicotine and 100 ppb TSNA), tobacco products having virtually any desired amount of nicotine and/or TSNAs can be manufactured. Tobacco products having various amounts of nicotine and/or TSNAs can be incorporated into tobacco use cessation kits and programs to help tobacco users reduce or eliminate their dependence on nicotine and reduce the carcinogenic potential.

For example, a step 1 tobacco product can be comprised of approximately 25% low nicotine/TSNA tobacco and 75% conventional tobacco; a step 2 tobacco product can be comprised of approximately 50% low nicotine/TSNA tobacco and 50% conventional tobacco; a step 3 tobacco product can be comprised of approximately 75% low nicotine/TSNA tobacco and 25% conventional tobacco; and a step 4 tobacco product can be comprised of approximately 100% low nicotine/TSNA tobacco and 0% conventional tobacco. A tobacco use cessation kit can comprise an amount of tobacco product from each of the aforementioned blends to satisfy a consumer for a single month program. That is, if the consumer is a one pack a day smoker, for example, a single month kit would provide 7 packs from each step, a total of 28 packs of cigarettes. Each tobacco use cessation kit would include a set of instructions that specifically guide the consumer through the step-by-step process. Of course, tobacco products having specific amounts of nicotine and/or TSNAs would be made available in conveniently sized amounts (e.g., boxes of cigars, packs of cigarettes, tins of snuff, and pouches or twists of chew) so that consumers could select the amount of nicotine and/or TSNA they individually desire. There are many ways to obtain various low nicotine/low TSNA tobacco blends using the teachings described herein and the following is intended merely to guide one of skill in the art to one possible approach.

To obtain a step 1 tobacco product, which is a 25% low nicotine/TSNA blend, prepared tobacco from an approximately 0 ppm nicotine/TSNA tobacco can be mixed with conventional Burley, Flue-cured, or Oriental in a 25%/75% ratio respectively to obtain a Burly tobacco product having 22,500 ppm nicotine and 6,000 ppb TSNA, a Flue-cured product having 15,000 ppm nicotine and 225 ppb TSNA, and an Oriental product having 7,500 ppm nicotine and 75 ppb TSNA. Similarly, to obtain a step 2 product, which is 50% low nicotine/TSNA blend, prepared tobacco from an approximately 0 ppm nicotine/TSNA tobacco can be mixed with conventional Burley, Flue-cured, or Oriental in a 50%/50% ratio respectively to obtain a Burly tobacco product having 15,000 ppm nicotine and 4,000 ppb TSNA, a Flue-cured product having 10,000 ppm nicotine and 150 ppb TSNA, and an Oriental product having 5000 ppm nicotine and 50 ppb TSNA. Further, a step 3 product, which is a 75%/25% low nicotine/TSNA blend, prepared tobacco from an approximately 0 ppm nicotine/TSNA tobacco can be mixed with conventional Burley, Flue-cured, or Oriental in a 75%/25% ratio respectively to obtain a Burly tobacco product having 7,500 ppm nicotine and 2,000 ppb TSNA, a Flue-cured product having 5,000 ppm nicotine and 75 ppb TSNA, and an Oriental product having 2,500 ppm nicotine and 25 ppb TSNA.

It should be appreciated that tobacco products are often a blend of many different types of tobaccos, which were grown in many different parts of the world under various growing conditions. As a result, the amount of nicotine and TSNAs will differ from crop to crop. Nevertheless, by using conventional techniques one can easily determine an average amount of nicotine and TSNA per crop used to create a desired blend. By adjusting the amount of each type of tobacco that makes up the blend one of skill can balance the amount of nicotine and/or TSNA with other considerations such as appearance and flavor., and smokeability. In this manner, a variety of types of tobacco products having varying level of nicotine and/or nitrosamine, as well as varying appearance and flavor and smokability can be created.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A cured tobacco comprising a genetic modification, a reduced amount of nicotine, and a collective content of N'-nitrosonornicotine (NNN), N'-nitrosoanatabine (NAT), N'-nitrosoanabasine (NAB), 4-(N-nitrosomethylamino)-1-(3-pyridyl)-1-butanone (NNK) of less than about 0.5 μg/g.

2. The cured tobacco of claim 1, wherein the collective content of NNN, NAT, NAB, and NNK is less than about 0.4 μg/g.

3. The cured tobacco of claim 1, wherein the collective content of NNN, NAT, NAB, and NNK is less than about 0.2 μg/g.

4. The cured tobacco of claim 1, wherein said cured tobacco is selected from the group consisting of Burley, Flue, or Oriental.

5. The cured tobacco of claim 4, wherein said cured tobacco is Burley.

6. The cured tobacco of claim 4, wherein said cured tobacco is Flue.

7. The cured tobacco of claim 1, wherein said tobacco comprises an exogenous quinolate phosphoribosyl transferase (QPTase) gene or a fragment thereof at least 13 nucleotides in length.

8. The cured tobacco of claim 1, wherein the amount of nicotine is less than about 0.5 μg/g.

9. The cured tobacco of claim 1, wherein the amount of nicotine is less than about 0.1 μg/g.

10. A tobacco product comprising the cured tobacco of claim 1.

11. The tobacco product of claim 10, wherein said tobacco product is selected from the group consisting of cigarettes, cigars, pipe tobacco, snuff, chewing tobacco, gum, and lozenges.

12. A method of making the tobacco product of claim 10, comprising providing the cured tobacco of claim 1 and preparing said tobacco product from said cured tobacco.

13. A method of reducing the amount of a TSNA or a TSNA metabolite in a human that uses tobacco, comprising providing said human the tobacco product of claim 10.

14. A blended tobacco product comprising the cured tobacco of claim 1.

15. The blended tobacco product of claim 14, wherein said tobacco product is selected from the group consisting of cigarettes, cigars, pipe tobacco, snuff, chewing tobacco, gum, and lozenges.

16. A method of making the blended tobacco product of claim 14, comprising providing the cured tobacco of claim 1 and preparing said tobacco product from said cured tobacco.

17. A tobacco use cessation kit comprising the cured tobacco of claim 1.

18. A method of reducing the carcinogenic potential of a tobacco product comprising providing the cured tobacco of claim 1 and preparing a tobacco product from said cured tobacco, whereby the carcinogenic potential of said tobacco product is thereby reduced.

19. A method of reducing the carcinogenic potential of side stream or main stream tobacco smoke in a human exposed to said side stream or main stream tobacco smoke, comprising providing the cured tobacco of claim 1 in a product that undergoes pyrolysis, wherein pyrolysis of said product results in side stream or main stream smoke comprising a reduced amount of TSNAs.

20. An improved tobacco product that contains Burley tobacco, wherein said improvement comprises a genetically modified Burley tobacco comprising a collective content of NNN, NAT, NAB, and NNK that is less than about 0.2 μg/g and an amount of nicotine that is less than about 0.5 mg.

* * * * *

UNITED STATES PATENT AND TRADEMARK OFFICE

CERTIFICATE OF CORRECTION

PATENT NO. : 6,907,887 B2

DATED : June 21, 2005

INVENTOR(S) : Mark A. Conkling

It is certified that error appears in the above-identified patent and that said Letters Patent is hereby corrected as shown below:

Column 53,

Lines 35 and 37, please delete "μg/g" and insert therefore, -- mg/g --.

Signed and Sealed this

Sixth Day of September, 2005

JON W. DUDAS

*Director of the United States Patent and Trademark Office*

UNITED STATES PATENT AND TRADEMARK OFFICE

CERTIFICATE OF CORRECTION

PATENT NO. : 6,907,887 B2 
DATED : June 21, 2005
INVENTOR(S) : Mark A. Conkling

It is certified that error appears in the above-identified patent and that said Letters Patent is hereby corrected as shown below:

Title page,
Item [56], References Cited, U.S.PATENT DOCUMENTS,
delete "2,728,603 8/1955" and insert -- 2,758,603 8/1956 --.

Column 54,
Line 43, delete "0.5 mg" and insert -- 0.5 mg/g --.

Signed and Sealed this

Thirty-first Day of January, 2006

JON W. DUDAS
*Director of the United States Patent and Trademark Office*